US011278475B2

(12) United States Patent
Truniger et al.

(10) Patent No.: US 11,278,475 B2
(45) Date of Patent: Mar. 22, 2022

(54) PERSONAL CARE COMPOSITION

(71) Applicant: Weidmann Holding AG, Rapperswil (CH)

(72) Inventors: Stefan Truniger, Pfäffikon ZH (CH); Tobias Wolfinger, Uznach (CH)

(73) Assignee: Weidmann Holding AG, Rapperswil (CH)

(*) Notice: Subject to any disclaimer, the term of this patent is extended or adjusted under 35 U.S.C. 154(b) by 111 days.

(21) Appl. No.: 16/603,289

(22) PCT Filed: Apr. 5, 2018

(86) PCT No.: PCT/EP2018/058749
§ 371 (c)(1),
(2) Date: Oct. 7, 2019

(87) PCT Pub. No.: WO2018/185230
PCT Pub. Date: Oct. 11, 2018

(65) Prior Publication Data
US 2021/0007941 A1  Jan. 14, 2021

(30) Foreign Application Priority Data
Apr. 7, 2017 (EP) .................................. 17165510

(51) Int. Cl.
*A61K 8/27* (2006.01)
*A61K 8/02* (2006.01)
(Continued)

(52) U.S. Cl.
CPC ............ *A61K 8/027* (2013.01); *A61K 8/0212* (2013.01); *A61K 8/0275* (2013.01); *A61K 8/042* (2013.01);
(Continued)

(58) Field of Classification Search
CPC ........................................................ A61K 8/27
See application file for complete search history.

(56) References Cited

U.S. PATENT DOCUMENTS 4,966,651 A  10/1990  Olson et al.
6,342,237 B1  1/2002  Bara
(Continued)

FOREIGN PATENT DOCUMENTS

CN  1922363 A  2/2007
CN  104144673 A  11/2014
(Continued)

OTHER PUBLICATIONS

U.S. Appl. No. 16/603,288, Stefan Truniger, et al., filed Oct. 7, 2019.
(Continued)

*Primary Examiner* — Benjamin J Packard
(74) *Attorney, Agent, or Firm* — Sughrue Mion, PLLC

(57) ABSTRACT

Disclosed are personal care compositions comprising a fibrous material of natural origin and obtained from plants. The fibrous material comprises micro-scaled and/or nano-scaled fibril agglomerates. Such compositions show pleasant skin feel and comfort during and after application, as well as fast drying and fast absorption into skin. The compositions obtained are also particularly well suited for the topical delivery of cosmetic and pharmaceutical active substances into skin. Additionally, a method to obtain said personal care composition is disclosed.

20 Claims, 4 Drawing Sheets

Figure 1:
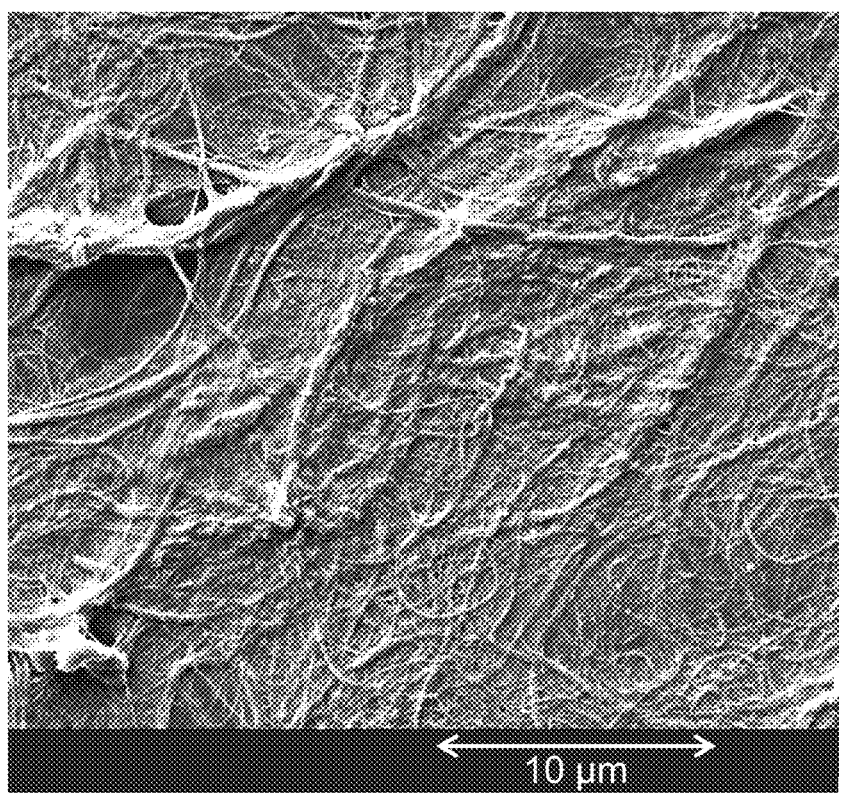

(51) Int. Cl.
*A61K 8/9789* (2017.01)
*A61K 8/04* (2006.01)
*A61K 8/73* (2006.01)
*A61Q 19/00* (2006.01)

(52) U.S. Cl.
CPC ............ *A61K 8/731* (2013.01); *A61K 8/9789* (2017.08); *A61Q 19/00* (2013.01)

(56) References Cited

U.S. PATENT DOCUMENTS

| | | | |
|---|---|---|---|
| 6,534,071 | B1 | 3/2003 | Tournilhac et al. |
| 2007/0196401 | A1 | 8/2007 | Naruse et al. |
| 2011/0293732 | A1 | 12/2011 | Nachtkamp et al. |
| 2013/0012695 | A1* | 1/2013 | Turner .................. D01D 1/065 536/56 |
| 2014/0154756 | A1 | 6/2014 | Nelson et al. |
| 2015/0110841 | A1 | 4/2015 | Wiechers et al. |
| 2017/0183555 | A1 | 6/2017 | Lillandt et al. |

FOREIGN PATENT DOCUMENTS

| | | |
|---|---|---|
| CN | 106460336 A | 2/2017 |
| DE | 20 2010 012 041 U1 | 12/2010 |
| EP | 0 819 787 A2 | 1/1998 |
| EP | 1 057 477 A1 | 12/2000 |
| EP | 1 243 250 A1 | 9/2002 |
| EP | 1 245 223 A1 | 10/2002 |
| ER | 0 120 471 A2 | 10/1984 |
| WO | 99/20241 A1 | 4/1999 |
| WO | 2006/048280 A1 | 5/2006 |
| WO | 2010/077170 A2 | 7/2010 |
| WO | 2011/004301 A1 | 1/2011 |
| WO | 2014/029909 A1 | 2/2014 |
| WO | 2015/180844 A1 | 12/2015 |
| WO | 2016/024046 A1 | 2/2016 |
| WO | 2016/166179 A1 | 10/2016 |

OTHER PUBLICATIONS

International Search Report in International Application No. PCT/EP2018/058749, dated Jun. 20, 2018.
Written Opinion in International Application No. PCT/EP2018/058749, dated Jun. 20, 2018.
International Preliminary Report on Patentability issued from the International Bureau in counterpart International Application No. PCT/EP2018/058749, dated Oct. 8, 2019.
M Rahimi Kord Sofia, et al., "A comparison of cellulose nanocrystals and cellulose nanofibres extracted from bagasse using acid and ball milling methods", Advances in Natural Sciences: Nanoscience and Nanotechnology, 2016, vol. 7, No. 035004, pp. 1-9 (10 pages total).
International Standard, ISO 13322-2, "Particle size analysis—Image analysis methods—Part 2: Dynamic image analysis methods", Nov. 1, 2006 (32 pages total).
Tobias Wolfinger, Nov. 2016 (244 pages total).
John R. Semancik, "Yield stress measurements using controlled stress rheometry", TA-Instruments, Thermal Analysis & Rheology, RH-058, 2014 (9 pages total).
International Standard ASTM D7836-13, "Standard Test Methods for Measurement of Yield Stress of Paints, Inks and Related Liquid Materials", 2013, pp. 1-3 (3 pages total).
Halbstoffe et al., EN ISO 4119, Apr. 1996 (2 pages total).
Alan Parker, et al., "Texture Profiling With the Vane: a General Method for Characterising the Rheology of Shear-Sensitive Soft Foods", 3rd International Symposium on Food Rheology and Structure, Jan. 2003, pp. 131-135 (6 pages total).
EN 20638, Sep. 1993 (2 pages total).
Schopper-Riegler-Verfahren, ISO 5267-1:1999, Jul. 2000, pp. 253-260 (10 pages total).
T271 pm-91, "Fiber length of pulp and paper by automated optical analyzer", Provisional Method, TAPPI, 1991 (4 pages total).
International Preliminary Report on Patentability with a Translation of Written Opinion in International Application No. PCT/EP2018/058744, dated Oct. 8, 2019.
International Search Report in International Application No. PCT/EP2018/058744, dated Jul. 5, 2018.
Written Opinion in International Application No. PCT/EP2018/058744, dated Jul. 5, 2018.

* cited by examiner

PERSONAL CARE COMPOSITION

CROSS REFERENCE TO RELATED APPLICATIONS

This application is a National Stage of International Application No. PCT/EP2018/058749 filed Apr. 5, 2018, claiming priority based on European Patent Application No. 17165510.3 filed Apr. 7, 2017.

TECHNICAL FIELD

The present invention relates to a personal care composition as well as to a method for producing such a personal care composition. Such personal care compositions are for example used in skin and hair care for example in the form of gels, cream-gels, soaps, shampoos, make-up, gel masks and the like.

PRIOR ART

A large variety of personal care compositions for use in skin and hair care is known. Personal care compositions are usually applied topically for cosmetic, cosmeceutical or pharmaceutical purposes. Desired properties of personal care compositions include, inter alia, a pleasant skin feel and comfort during and after application as well as fast drying properties. Thus, fast absorption by the skin and excellent film-forming properties are important characteristics of personal care compositions.

Many personal care compositions contain natural and/or synthetic fibers due to their numerous beneficial sensory features, such as a pleasant application on skin, a minimal wet feeling, a slight cooling effect, the absence of greasiness as well as the absence of a tacky feeling. Furthermore, fibers can be used as a binding ingredient and usually have good drying properties and in many cases have an anti-irritant effect on the skin.

EP 1 243 250 discloses the use of fibers as an anti-irritant ingredient in cosmetic or dermatological compositions. A broad selection is proposed, including synthetic fibers and fibers of natural origin.

U.S. Pat. No. 6,342,237 B1 discloses a make-up composition in which a fiber is combined with an aqueous dispersion of at least one film-forming polymer.

WO 99/20241 A1, U.S. Pat. No. 6,534,071 B1, EP 1 245 223 A1 and WO 2016/166179 A1 also each disclose the use of cellulose fibrils in personal care compositions. The fibrils present in these compositions are individually isolated and separated from each other, which require homogenization of the composition by means of a high-shear or a high-pressure homogenization means.

Further, personal care compositions are known comprising microcrystalline cellulose. Microcrystalline cellulose is generated by subjecting cellulose to pure acid hydrolysis. Amorphous regions of microfibrillated cellulose are selectively hydrolysed as they are more susceptible to being attacked by acids compared to the crystalline domains. Consequently, these microfibrils break down in shorter crystalline parts with a high degree of crystallinity. In contrast, microfibrillated cellulose still consists of amorphous and crystalline regions (Adv. Nat. Sci.: Nanosci. Nanotechnol. 7 (2016), 035004).

Actually, in many cases and especially when using the fibrils as described in the state of the art listed above, the compositions obtained do not provide the desired skin feel and comfort during application, but are characterized by a wet feeling, long drying times and the occurrence of pilling when applied to the skin. These undesired properties have made the implementation of natural fibrils in personal care slow and difficult.

Furthermore, EP 0 819 787 A2 discloses the general use of cellulose fibrils having a certain length and diameter as a mixing stabilizer in a large variety of applications. The use of the fibrils in personal care compositions, however, is not disclosed in this document.

SUMMARY OF THE INVENTION

It is an object of the present invention to provide a personal care composition which has improved properties with respect to its application to skin and/or to hair, in particular as concerns the feeling as sensed by the user.

In order to solve this object, the present invention provides a personal care composition comprising a fibrous material of natural origin and obtained from plants, wherein the fibrous material comprises micro-scaled and/or nano-scaled fibril agglomerates.

The provision of the fibrous material comprising the micro-scaled and/or nano-scaled fibril agglomerates in the personal care composition results in a well-structured and non-irritant personal care composition with good drying properties.

Furthermore, it has been found that the personal care composition according to the present invention shows a good compatibility with a broad selection of known cosmetic and pharmaceutical ingredients, and that the formulation of these cosmetic and pharmaceutical ingredients may be performed without the aid of high shear rotor-stator or high pressure homogenizers, and without requiring heating at any time of the formulation process.

The fibrous material comprises micro-scaled and/or nano-scaled fibril agglomerates, which means that the individual fibers and in particular the micro fibrils of the original cellulose material are comminuted and are present at least partially or completely separated from each other, wherein the separated micro fibrils in particular form fibril agglomerates due to mutual association. The average lengths of these agglomerates are indicated further below. The micro fibrils being present within the fibril agglomerates are completely separated from the original fiber structure of the cellulose and are interconnected with each other due to mutual adherence, such that they form a common structure, in particular a network.

Within the micro-scaled and/or nano-scaled fibril agglomerates, the individual micro fibrils are strongly interacting, which means that the dissociation of the fibrils constituting the agglomerates from each other would require the use of e.g. a high-pressure homogenizer, typically by passing a dispersion of a liquid, which preferably is an aqueous medium, and of the fibrous material comprising the micro-scaled and/or nano-scaled fibril agglomerates several times through said high-pressure homogenizer. Such high-pressure homogenizer conditions are usually not applied to the personal care compositions in the context of the present invention.

As already mentioned, due to the presence of the micro-scaled and/or nano-scaled fibril agglomerates, the personal care composition has good drying properties. In particular, it was noticed, that the composition is fast drying, and a fast absorption is taking place. Furthermore, the personal care composition normally has good film-forming properties. Under "fast drying" is preferably meant a drying process that is fast enough, so that the perception of a wet skin feeling disappears within about 30 seconds, more particularly within about 20 seconds after the composition has been applied to the skin. Under "fast absorption" is preferably meant that the composition does not leave any noticeable residues on skin after about 20 seconds, more particularly after about 10 seconds, wherein the presence of residues is typically associated with an oily feeling, a fatty feeling, a tacky feeling or the sensation of material build-up on the skin. Under "film-forming properties" is preferably meant the ability of the composition to form a film upon drying, said film conferring a smooth, silky aspect to the skin or to the hair and providing the user with the impression of an enhanced protective action of the composition against environmental nuisances.

In a further development of the invention, the micro-scaled and/or nano-scaled fibril agglomerates, more preferably the fibrous material, and even more preferably the personal care composition, is substantially free of visible isolated fibrils, in particular completely free of visible isolated fibrils. It has been found that by the absence of visible isolated fibrils in the micro-scaled and/or nano-scaled fibril agglomerates, more preferably in the fibrous material, and even more preferably in the personal care composition, a particularly silky feel of the personal care composition on the skin can be achieved. This feel can also be noticed in a composition that is used for hair care, for example when spreading the product in the hair with the hands. The user has the impression of an enhanced protective action of the composition against environmental nuisances.

Preferably, the personal care composition is meant to be "substantially free of visible isolated fibrils", if essentially all possibly present fibrils in the personal care composition are associated into micro- and/or nano-scaled fibril agglomerates. In particular, the personal care composition is meant to be "substantially free of visible isolated fibrils", if the visible isolated fibrils represent preferably no more than 5 percent, more preferably no more than 1 percent, of the total number of the visible particles of the personal care composition.

Preferably, the fibrous material is meant to be "substantially free of visible isolated fibrils", if essentially all possibly present fibrils in the fibrous material are associated into micro- and/or nano-scaled fibril agglomerates. In particular, the fibrous material is meant to be "substantially free of visible isolated fibrils", if the visible isolated fibrils represent preferably no more than 5 percent, more preferably no more than 1 percent, of the total number of the visible particles of the fibrous material.

Preferably, the micro- and/or nano-scaled fibril agglomerates are meant to be "substantially free of visible isolated fibrils", if essentially all possibly present fibrils in the micro- and/or nano-scaled fibril agglomerates are associated into the micro- and/or nano-scaled fibril agglomerates. In particular, the micro- and/or nano-scaled fibril agglomerates are meant to be substantially free of visible isolated fibrils, if the visible isolated fibrils represent preferably no more than 5 percent, more preferably no more than 1 percent of the total number of the visible micro- and/or nano-scaled fibril agglomerates.

Isolated fibrils are meant to be visible, if they can easily be identified as such, when the material is observed by means of an electron microscope, such as a transmission electron microscope, or scanning electron microscope at a magnification of 10'000 and a resolution of 100 nanometers.

Without being bound by theory, it is believed that the remarkable sensory features mentioned hereinabove are linked at least partially to the fact that the composition comprises the micro-scaled and/or nano-scaled fibril agglomerates. These sensory features are further enhanced if the composition is substantially free of visible isolated fibrils, preferably completely free of visible isolated fibrils. Such compositions usually have a water retention and a water release behavior that is in many cases favorable with respect to its use in personal care products.

The average length of the micro-scaled fibril agglomerates is preferably in the range of 500 nm-1000 µm, more preferably in the range of 500 nm-600 µm, even more preferably in the range of 500 nm-200 µm. The average length of the nano-scaled fibril agglomerates is preferably in the range of 10 nm to 500 nm. The assessment of the average length of the micro-scaled fibril agglomerates is preferably carried out by means of the standard ISO 13322-2, 1. Edition of Nov. 1, 2006 which is incorporated herein as reference. Personal care compositions comprising such micro-scaled and/or nano-scaled fibril agglomerates have especially good properties.

Preferably at least 1%, more preferably at least 10%, even more preferably at least 20%, even more preferably at least 40%, even more preferably at least 50%, even more preferably at least 60%, even more preferably at least 70%, even more preferably at least 80%, even more preferably at least 90%, most preferably 100% of the total number of particles of the fibrous material comprise an average length in the range of 500 nm-1000 µm, more preferably in the range of 500 nm-600 µm, even more preferably in the range of 500 nm-200 µm. The particles of the fibrous material not only comprise the micro-scaled and/or nano-scaled fibril agglomerates, but also possibly present fibrils as well as possibly further constituents of the fibrous material. Said percentages of the average lengths are preferably determined by the standard ISO 13322-2, 1. Edition of Nov. 1, 2006. Personal care compositions comprising such a fibrous material have especially good properties.

Preferably at least 1%, more preferably at least 10%, even more preferably at least 20%, even more preferably at least 40%, even more preferably at least 50%, even more preferably at least 60%, even more preferably at least 70%, even more preferably at least 80%, even more preferably at least 90%, most preferably 100% of the total number of particles of the fibrous material comprises an average length in the range of 10 nm-500 nm. Personal care compositions comprising such a fibrous material have especially good properties.

The fibrous material comprising the micro-scaled and/or nano-scaled fibril agglomerates comprises preferably a surface of 40-450 $m^2/g$, more preferably a surface of 50-400 $m^2/g$, even more preferably a surface of 60-400 $m^2/g$, most preferably a surface of 80-350 $m^2/g$. Personal care compositions comprising such a fibrous material have especially good properties. For the measuring of said surface, preferably the following method comprising the steps "Sample preparation I", "Sample preparation II" and "Performance of the nitrogen adsorption measuring/calculation of the surface of the fibrous material comprising the micro-scaled and/or nano-scaled fibril agglomerates" is used:

Sample Preparation I

About 20 g of a fiber dispersion comprising 2 wt % of the fibrous material comprising the micro-scaled and/or nano-scaled fibril agglomerates are weighted into a 50 ml Falcon tube. Ethanol (94%) is added till the volume of 50 ml of the Falcon tube is reached. After that, the content of the Falcon tube is mixed by means of a vortex mixer. After that, the sample is centrifugated by means of a centrifuge (e.g. Typ Hettich Rotina 380 mit 6-fach Winkelrotor 45°) at 5000 l/min during 10 minutes. After that, the filtrate is removed and again ethanol (94%) is filled into the empty volume. After that, the content of the Falcon tube is stirred with a glass rod. After that, the sample is loosened again by means of a vortex mixer and centrifugated at the same parameters as mentioned above. This procedure is repeated 5 times.

Subsequently, the residual moisture of the sample is determined by drying the sample by means of supercritical $CO_2$ in a device such as a Tousimis Autosamdri 931.

Sample Preparation II

The sample, which is dewatered according to the method according to sample preparation I, is weighted into a glass tube. Before weighting the sample into the glass tube, the glass tube is dried and weighted when it is empty. After that, the sample comprised by the glass tube is degassed during at least 24 hours at least 105° C.

Performance of the Nitrogen Adsorption Measuring/Calculation of the Surface of the Fibrous Material Comprising the Micro-Scaled and/or Nano-Scaled Fibril Agglomerates The glass tube comprising the degassed sample, wherein the degassing was performed by means of sample preparation II, is now arranged in a suitable measuring device, such as a Micromeritics 3Flex Version 3.01, in order to determine the nitrogen sorption isotherm. The sample mass is for example 0.0777 g, but the sample mass can deviate from said sample mass because of the type of measuring device or because of the specific sample. The nitrogen and the helium which are used for the performance of the measuring have a purity of 99,999%. The result of the measuring is calculated to one decimal place in $m^2/g$ ($m^2/lg$). The calculated value of the result is based on the BET—method according to Brunauer, Emmett and Teller which is known by person skilled in the art.

The D90-value of the length of the particles comprised by the fibrous material comprising the micro-scaled and/or nano-scaled fibril agglomerates is preferably in the range of 1-200 µm, more preferably in the range of 30-150 µm, even more preferably in the range of 40-140 µm. The D90-value of the length of the particles comprised by the fibrous material indicates the maximal length of 90% of the particles of the fibrous material. The calculation of the D90-value is known by the person skilled in the art. The length of the particles is preferably determined by means of the standard ISO 13322-2, 1. Edition of Nov. 1, 2006. Personal care compositions comprising such a fibrous material have especially good properties.

The D90-value of the thickness of the particles comprised by the fibrous material comprising the micro-scaled and/or nano-scaled fibril agglomerates is preferably in the range of 0.5-20 µm, more preferably in the range of 1-10 µm µm, even more preferably in the range of 1-8 µm. The D90-value of the thickness of the particles comprised by the fibrous material indicates the maximal thickness of 90% of the particles of the fibrous material. The calculation of the D90-value is known by the person skilled in the art. The thickness of the particles is preferably determined by means of the standard ISO 13322-2, 1. Edition of Nov. 1, 2006. Personal care compositions comprising such a fibrous material have especially good properties.

The water retention value of the fibrous material comprising the micro-scaled and/oder nano-scaled fibril agglomerates is preferably in the range of 100-700 wt %, more preferably in the range of 150 wt %-600 wt %, even more preferably in the range of 170 wt %-500 wt %, wherein the water retention value is determined according to the information mentioned in «T. Wolfinger, Dreidimensionale Strukturanalyse and Modellierung des Kraft-Dehnungsverhaltens von Fasergefügen, TU Dresden, Fakultät Umweltwissenschaften, Dissertation submitted in November 2016». Personal care compositions comprising such fibrous material have especially good properties.

In a particularly preferred embodiment, the fibrous material comprising the micro-scaled and/or nano-scaled fibril agglomerates comprises at least one, preferably several, more preferably all of the properties selected from the group comprising the average length of the micro-scaled and/or nano-scaled fibril agglomerates, the surface of the fibrous material, the percentages of the average length of the particles of the fibrous material, the water retention value of the fibrous material, the D90-value of the length of the particles of the fibrous material, the D90-value of the thickness of the particles of the fibrous material. All the possibilities of combination are not explicitly mentioned, but are considered as disclosed. Personal care compositions comprising such a fibrous material have especially good properties.

Preferably the fibrous material of natural origin is obtained from plants which are for example perennial plants, such as trees, comprising fruit bearing trees and parts thereof, shrubs and parts thereof, seaweed and annual plants selected from the group comprising cereals, grass and fibrous vegetables, such as peas and pulses.

The fibrous material and in particular the micro-scaled and/or nano-scaled fibril agglomerates are even more preferably obtained from hardwood, more preferably from the Eucalyptus tree, in particular from the Eucalyptus Urograndis tree, and/or from the beech tree. It has been found that the use of fibrous material comprising micro-scaled and/or nano-scaled fibril agglomerates that originates from the Eucalyptus tree, particularly from the Eucalyptus Urograndis tree, and/or from the beech tree results in a personal care composition with particular beneficial properties. Due to the large portion of xylose in these trees, a personal care composition is obtained that has a particularly pleasant, smooth and silky skin feel. Furthermore, Eucalyptus trees and beech trees are well suited due to their good availability.

Preferably, the fibrous material and in particular the micro-scaled and/or nano-scaled fibril agglomerates contain more than 10 wt % xylose, more preferably more than 15 wt % xylose, and most preferably more than 20 wt % xylose, referred to the total weight of the fibrous material, in particular of the dry fibrous material, or referred to the total weight of the micro-scaled and/or nano-scaled fibril agglomerates, in particular of the dry micro-scaled and/or nano-scaled fibril agglomerates, respectively. It has surprisingly been found that the amount of xylose in the fibrous material, in particular in the micro-scaled and/or nano-scaled fibril agglomerates, is particularly responsible for the advantageous sensory features of the personal care composition. In this context, it has been found that a large portion of xylose in the fibrous material, in particular in the micro-scaled and/or nano-scaled fibril agglomerates, leads to a particularly smooth and silky feel of the composition. Surprisingly, it was found that a higher xylose content in the microscaled and/or nano-scaled fibril agglomerates provides a better stabilization for the composition, in particular for an emulsion, than respective fibril agglomerates with no xylose or a low xylose content. A homogenous composition is obtained leading to the smoother and silky feel. A better homogeneity was also observed compared to compositions made of microcrystalline cellulose. The amount of xylose comprised by the fibrous material is preferably measured according to the information provided by «T. Wolfinger, Dreidimensionale Strukturanalyse and Modellierung des Kraft-Dehnungsverhaltens von Fasergefügen, TU Dresden, Fakultät Umweltwissenschaften, Dissertation submitted in November 2016».

According to an aspect of the invention, the fibrous material comprising the micro-scaled and/or nano-scaled fibril agglomerates is obtained from chemically untreated plant pulp. Chemically untreated plant pulp refers to plant pulp where the cellulosic groups have not been modified Preferably, the personal care composition comprises a liquid. According to preferred embodiment, the liquid comprises water. More preferably, the liquid is water.

According to another preferred embodiment, the liquid is a protic liquid. Preferably, the protic liquid comprises water, more preferable the protic liquid is water.

Preferably, at least a portion of the fibrous material is arranged, preferably dispersed, in the liquid, more preferably all the fibrous material is arranged, preferably is dispersed, in the liquid.

Preferably, at least a portion of the micro-scaled and/or nano-scaled fibril agglomerates of the fibrous material, more preferably all the micro-scaled and/or nano-scaled fibril agglomerates of the fibrous material, are arranged, preferably are dispersed, in the liquid.

When being arranged, preferably dispersed, in a liquid, which liquid is for example water or which liquid is for example a liquid comprising water, usually a mutual association, i.e. attraction or adherence or interaction of the individual micro-scaled and/or nano-scaled fibril agglomerates takes place, such that a gel-like material is obtained. Thus, the micro-scaled and/or nano-scaled fibril agglomerates, particularly if they are arranged in a liquid comprising water, more particularly if they are arranged in a liquid which is water, effectuate a structure, also referred to as texture, which is desired in many personal care compositions. Thus, the personal care composition preferably comprises water and the fibrous material comprising micro-scaled and/or nano-scaled fibril agglomerates, wherein the micro-scaled and/or nano-scaled fibril agglomerates are associated. The associated micro-scaled and/or nano-scaled fibril agglomerates allow particularly well to retain e.g. functional ingredients. A further particularly beneficial feature is that these textures remain unaffected upon addition of a broad selection of cosmetic, pharmaceutical ingredients and electrolytes. Materials that can be achieved extend from fluid materials, to self-standing gel-like materials.

Usually, if the micro-scaled and/or nano-scaled fibril agglomerates are arranged in a liquid, which preferably is an aqueous medium, which more preferably is water, the individual micro-scaled and/or nano-scaled fibril agglomerates are weakly interacting and associated, which means that they may be dissociated from each other under moderate shear conditions, for example at shear rates higher than $0.1\ s^{-1}$ or higher than $1\ s^{-1}$, at 20° C., or stresses higher than 10, or higher than 50, or higher than 100 Pa, at 20° C., depending on the strength of the interaction between the micro-scaled and/or nano-scaled fibril agglomerates and the level of micro-scaled and/or nano-scaled fibril agglomerates in the composition. Dissociation of the micro-scaled and/or nano-scaled fibril agglomerates from each other makes the composition starting to flow under the applied stress.

The personal care composition according to the invention is preferably a self-standing, gel-like material at room temperature, and also for example at 20° C. or 25° C. or 30° C.

In the context of the present invention, the term "self-standing, gel-like material" preferably is used to describe a material which does essentially not flow when submitted to low shear stresses. Such a material may, however, flow when submitted to higher shear stresses. The stress at which the material starts to flow is referred to as the yield stress. The yield stress may be measured using the vane technique, where a 4 or 6 blade vane is immersed in the composition, maintained at constant temperature, and rotated extremely slowly, typically below 0.5 rpm, for example 0.1 rpm, while the stress required to maintain a constant rotational speed is measured using a rheometer, as a function of time. Once the composition has been deformed by the vane in such a way that the stress applied exceeds the yield stress of the composition, the composition starts to flow and the force decreases. The yield stress is determined at the maximum of the stress-time curve. More information about the vane method may be found in A. Parker & F. Vigouroux, "Texture Profiling with the Vane: a general method for characterizing the texture of soft food", *Proc. 3rd Int. Symp. Food Rheol. Structure*, P. Fischer, I. Marti and E. J. Windhab (edts), 131-136, 2003. Other methods suitable for measuring the yield stress of the compositions according to the invention are described in J. R. Semancik, "Yield stress measurements using controlled stress rheometry", TA-Instruments documentation RH-058, available under http://www.tainstruments.com/pdf/literature/RH058.pdf web site and in the International Standard ASTM D7836-13, "Standard Test Methods for Measurement of Yield Stress of Paints, Inks and Related Liquid Materials", 2013.

The compositions according to the invention have preferably a yield stress at 20° C. of about 10 Pa and more, more preferably about 50 Pa and more and most preferably about 100 Pa and more.

The personal care compositions according to the present invention have preferably a viscosity at 20° C. of about 100 Pa·s and more, more particularly of about 1000 Pa·s and more, at a shear rate of about $0.01\ s^{-1}$ and exhibit a pronounced drop of viscosity by at least one order of magnitude when submitted to increasing shear rate from $0.01\ s^{-1}$ to $100\ s^{-1}$. The yield stress and the viscosity may be measured by performing rheological measurements with a rheometer equipped with a thermostat, for example a Thermo Scientific HAAKE RheoStress 6000 or a TA Instruments CSL2 Controlled Stress Rheometer, or equivalent.

Advantageously, the personal care composition comprises from 0.1 to 30 wt %, preferably from 0.5 to 20 wt %, more preferably from 1 to 10 wt %, of the fibrous material comprising the micro-scaled and/or nano-scaled fibril agglomerates, referred to the total weight of the composition. It will be easily understood by the skilled person that the level of fibrous material comprising the micro-scaled and/or nano-scaled fibril agglomerates may be chosen depending on the desired texture of the personal care composition. Hence, for example, it may be desirable that the personal care composition is not too viscous or not too liquid, depending on the application of the personal care composition. Preferably, the amount of fibrous material comprised by the personal care composition is determined by the standard ISO 4119, 1995.

In the context of the present invention, the term "personal care composition" preferably comprises generic skin care and hair care products, such as soaps, cleansing compositions, shower gels, shampoos, hair conditioners, and the like. It preferably also comprises cosmetic products, such as creams, body milks, facial masks, make-up and decorative products, and the like. The term "personal care composition" also comprises cosmeceutical and pharmaceutical products that are usually applied topically.

In a preferred embodiment, the personal care composition according to the present invention is used as a gel, a jelly, a cream-gel, a serum, a sorbet, a soufflé or a mousse. These particular states of matter differentiate from other products like creams, ointments, and milks in that said states of matter are characterized by different textures and aspects. In particular, these states of matter are characterized in that they retain their shape and thickness over time and as long as they have not undergone any shear stresses, but may flow and spread under the action of shear stresses, for example by rubbing the composition on the skin or on the hair. Self-standing behaviour at rest and flow behaviour under shear stress is typical of reversible network formation in the system, whereas a self-standing gel without flow behaviour under shear stress is typical of irreversible network formation in the system.

Preferably, the state of matter of the personal care compositions according to the present invention is characterized by a reversible behaviour.

A personal care composition which is easy to produce and has particularly advantageous properties is preferably achieved, if the fibrous material comprising the micro-scaled and/or nano-scaled fibril agglomerates is obtained by performing at least the steps of:

a.) comminuting dry pulp by mechanical means;
b.) dispersing said dry comminuted pulp in a liquid; and
c.) further comminuting the dispersed pulp in the liquid to form a mixture of the fibrous material comprising the micro-scaled and/or nano-scaled fibril agglomerates and the liquid, in particular by means of a mineral material, wherein the mixture preferably is substantially free of visible isolated fibrils, more preferably completely free of visible isolated fibrils.

By performing at least the steps a.), b.) and c.), a mixture comprising the liquid and the fibrous material comprising micro-scaled and/or nano-scaled fibril agglomerates can be produced which preferably is free of visible isolated fibrils, which is more preferably completely free of visible isolated fibrils. This mixture itself preferably is used as a basis to produce the personal care composition which is well structured and non-irritant with good drying properties.

The dry pulp of step a.) is preferably a dry pulp sheet or flash-dried pulp

Preferably, step a.) is performed without the addition of liquid, i.e. the dry pulp, in particular the dry pulp sheet or the flash-dried pulp, is comminuted without the addition of a liquid.

The pulp of step a.) is regarded to be dry, if it has a water content that is normal for the corresponding type of pulp, i.e. there are no substantial additions of water or any other liquid. Small additions of water or of another liquid can be present, as long as they do not substantially influence the total weight of the pulp material, i.e. preferably by not more than 15 wt %, more preferably by not more than 10 wt %, even more preferably by not more than 5 wt %. The pulp material is particularly not regarded to be dry in cases, in which it is dispersed in a liquid. The dry pulp preferably comprises at the maximum 15 wt %, more preferably at the maximum 10 wt %, even more preferably 1-9 wt %, most preferably 5 wt % to 8 wt % of water, referred to the total weight of the dry pulp, wherein the water content is measured preferably by means of the standard EN 20638, September 1993.

The use of dry pulp in step a.) has the advantage that metal particles, that might occur during comminution due to abrasion, do not enter into the fibers together with the liquid. As a consequence, possible metal particles that are present during comminution can be separated from the obtained mixture easily. The presence of metal particles in the mixture is problematic particularly to the greying of the fibrous material and hence of the personal care composition as a result thereof. Moreover, particularly in pharmaceutical products, food products or cosmetic products, the presence of metal particles in the product is often inacceptable.

The further comminuting of step c.) is performed for example by means of mechanical means such as high pressure homogenization or grinding with mineral grinding stones such as ball milling.

Preferably, at least 10 wt %, more preferably at least 20 wt %, even more preferably at least 40 wt %, even more preferably at least 60 wt %, even more preferably at least 80 wt %, even more preferably at least 90 wt %, even more preferably at least 95 wt %, most preferably 100 wt %, of the total weight of the fibrous material of the mixture is formed by micro-scaled and/or nano-scaled fibril agglomerates.

Preferably, the personal care composition comprises one or more functional ingredients, selected from the group comprising cleansing ingredients, texturing ingredients, softening ingredients, emollients, hydrating ingredients, lubricating ingredients, smoothening ingredients, soothing and relaxing ingredients, exfoliating ingredients, cell renewal and anti-aging ingredients, draining ingredients, remodeling ingredients, free-radical scavengers, structuring ingredients, anti-oxidant; decorative ingredients, skin levelling ingredients, epilating ingredients, whitening ingredients, deodorants, antibacterial or bacteriostatic ingredients, biological preservatives.

The one or more functional ingredient is advantageously selected from the group comprising synthetic polymers, natural polymers, solvents, mineral and vegetal oils, surfactants, fatty acid and fatty alcohol esters, C10-C24 fatty acids and their salts, C10-C24 fatty alcohols, alpha and beta hydroxy acids and their salts, salicyclic acid and its salts, dicarboxylic acids and their salts, pyrrolidone carboxylic acid, proteins and peptides, collagen, glycolipides; phospholipides; sphingolipides, sterols and steroids, glycerine ethoxylate, calcium glyconate, polidocanol, urea, allantoin, caffein, pyroctone olamine, acetyl carnitine, amino acids and their derivatives, quaternary amines, alpha-lipoic acid, alkaline base, flavonoids and isoflavonoids, polyphenols, anthocyanins, minerals, organic dyes and pigments, vitamins and their derivatives, terpenes and their derivatives, sesquiterpenes and their derivatives, triterpenes and their derivatives, ubiquinones, sequestering ingredients, UV-absorbing ingredients, antioxidants, waxes and butters, carbohydrates and sugar alcohols, and their derivatives, deodorizing ingredients, mineral and vegetal particulates, biological preservatives, plant extracts, juices, essential oils and fragrances. A more comprehensive but still not limited list of functional ingredients is given hereinafter.

Preferably, the personal care composition comprises at least one synthetic or natural hydrophilic polymer. The at least one synthetic or natural hydrophilic polymer is preferably a copolymer or a terpolymer selected from the group comprising vinylpyrrolidone/acrylate copolymers, copolymers and cross-polymers derived from alkyl (meth)acrylates, (meth)acrylic acids and acrylamidodimethyltauric acid and their salts, vinylpyrrolidone/acrylamido alkylsulphonic acid copolymers and their salts, xanthan gum, dehydroxanthan gum, guar gum, gum Arabic, Accacia gum, Sclerotium gum, Ceratonia siliqua gum; pullulans, glucans, glycoaminoglycanes, carraghenans, pectins, alginates, hyaluronic acid and its salts, sodium hyaluronate cross-polymers, chitosan, and mixtures thereof; and wherein the level of polymer in the composition is particularly in the range of 0.05 and 10 wt %, more particularly in the range of about 0.1 and about 7 wt %, still more particularly in the range of about 0.25 and about 5 wt %, for example about 0.5 wt %, about 1 wt %, about 2.5 wt % or about 4 wt % referred to the total weight of the composition.

Furthermore, the personal care composition can comprise one or more surfactants. In a preferred embodiment, the personal care composition of the invention is surfactant-free.

As already mentioned, the micro-scaled and/or nano-scaled fibril agglomerates and the possibly present super-structures formed therefrom are usually remarkably compatible with a broad selection of cosmetic ingredients, so that the incorporation of these ingredients in particular into aqueous systems comprising the agglomerates does not require the use of high shear mixing devices, such as rotor-stator mixers, or high pressure homogenizing devices, and can be performed at room temperature, for example at 20 or 25° C. For the same reason, it is also possible to obtain surfactant-free compositions by using these micro-scaled and/or nano-scaled fibril agglomerates. The other ingredients of the personal care compositions according to the present invention, can be functional formulation ingredients providing texturing, viscosity control, stability and the like, and/or cosmetic ingredients providing cleansing; softening; emolliency; hydration; lubrication; smoothening; soothing; exfoliating; relaxation; cell renewal and anti-aging action; draining, remodeling, free-radical scavenging, structuring; styling, anti-oxidant action; decorative effects, such as gloss, skin evenness or hair volume; epilation, whitening; smell; deodorancy; antibacterial or bacteriostatic effect, biological preservation, and the like.

Exemplary useful ingredients are listed hereunder, wherein some of these ingredients may provide one or more of the aforementioned functions.

Synthetic hydrophilic polymers are useful functional ingredients in the context of the present invention and may be selected from the group comprising
- polymer and copolymers of vinyl and allyl monomers, for example polyvinylpyrrolidone; vinylpyrrolidone/acrylate copolymers; vinylpyrrolidone/vinyl acetate copolymers; polyvinylalcohol, more particularly hydrolyzed polyvinylacetates having a degree of hydrolysis in the range of 85 and 92%; vinyl ester homopolymers and copolymers, such as vinyl pivalate, vinyl versatate; polyvinyl alkyl amines, such as polyvinylmethylamine; quaternized polyvinyl alkyl amines, vinyl pyridine and quaternized vinyl pyridine, vinyl imidazoline, vinyl imidazole, vinyl imidazolinium, dimethyldiallyl ammonium chloride; and vinyl sulphonate homopolymers and copolymers;
- polyamines and polyimines;
- ethoxylated polyamines;
- polymers, copolymers and cross-polymers derived from alkyl (meth)acrylates, such as methyl methacrylate, ethyl methacrylate, 2-ethyl-hexyl acrylate, lauryl methacrylate, C10-C30 alkyl acrylate, and the like, hydroxyalkyl (meth)acrylate, such as 2-hydroxypropyl acrylate and 2-hydroxypropyl methacrylate, and the like; acrylamidodimethyl taurate; aryl (meth)acrylates, such as phenyl acrylate and benzyl acrylate, (meth)acrylic acids and acrylamidodimethyltauric acid and their salts, such as sodium and potassium (meth)acrylates, sodium acryloyldimethyltaurate; (meth)acrylamides; N-alkyl (meth)acrylamides, such as N,N-dimethylaminoalkyl methacrylate; quaternized N-alkyl (meth)acrylamides, such as methacrylamidopropyl-trimethylammonium chloride; acrylamidoethyltrimonium chloride; acrylamidolauryltrimethylammonium chloride; and (meth)acrylamido alkyl sulphonates;
- maleic acid anhydride copolymers with vinyl ethers, such as maleic anhydride/methyl vinylether copolymers;
- polyurethanes, such as anionic, cationic non-ionic and amphoteric polyurethanes; polyurea;
- mixed copolymers, for example polyurethanes with polyesters, polyacrylates, with polyvinylpyrrolidone; polyesters; polyester/polyamide copolymers; vinylpyrrolidone/acrylamido alkylsulphonic acid copolymers, such as vinylpyrrolidone/acrylamido 2-methylpropane sulphonic acid copolymers;
- mixtures thereof.

Natural hydrophilic biopolymers or modified biopolymers that are useful for the sake of the present invention may be selected from the group comprising modified celluloses, such as carboxy methyl cellulose, hydroxyethyl cellulose, hydroxyethyl cellulose/lauryl-dimethylammoniumepoxy condensat, hydroxypropyl cellulose, cationic cellulose (for example Polyquaternium-4), cellulose gum, starch, modified starch, such as hydrolized starch octenyl succinate, dextrins, maltodextrins, trehalose, xanthan gum, dehydro-xanthan gum, guar gum, gum Arabic, accacia gum, sclerotium gum, ceratonia siliqua gum, guar hydroxypropyl trimethylammonium chloride, pullulans, glycans, glycoaminoglycanes, carraghenans, alginates, hyaluronic acid and its salts, sodium hyaluronate cross-polymers, glycosaminoglycanes (Chondroitin), chitosan, and mixtures thereof.

Hydrophobic polymers that are useful for the sake of the present invention may be selected from the group comprising alkyldimethylsiloxanes; polymethylsilsesquioxanes; vinyl dimethicone crosspolymers; alkylene/vinyl pyrrrolidone copolymers; polyethylene; styrene polymers and copolymers, such as styrene/ethylene/butene/styrene, styrene/ethylene/styrene and styrene/butylene/styrene block elastomer copolymers; polyisobutylene; and mixtures thereof.

Amphiphilic polymers that are useful for the sake of the present invention may be selected from the group comprising polyethylene glycol/castor oil copolymers; ethylene glycol/propylene glycol diblock and triblock copolymers; sorbitan oleate alkyl glucoside crosspolymers; polydimethyl siloxane polymers modified with polyoxyalkylene or polyamine moieties, such as polyethylene glycol/polypropylene glycol dimeticone; and mixtures thereof.

Mineral structuring ingredients that are useful for the sake of the present invention may be selected from the group comprising clays and silicates, such as bentonites and laponites.

In a preferred embodiment, the personal care composition of the invention comprises at least one hydrophilic copolymer or terpolymer selected from the group comprising vinylpyrrolidone/acrylate copolymers, copolymers and cross-polymers derived from alkyl (meth)acrylates, (meth) acrylic acids and acrylamidodimethyltauric acid and their salts, vinylpyrrolidone/acrylamido alkylsulphonic acid copolymers, xanthan gum, dehydro-xanthan gum, guar gum, gum Arabic, accacia gum, sclerotium gum, ceratonia siliqua gum; pullulans, glucans, glycoaminoglycanes, carraghenans, alginates, pectins, hyaluronic acid and its salts, sodium hyaluronate cross-polymers, chitosan, and mixtures thereof.

In a preferred embodiment, the level of polymer in the composition is particularly in the range of 0.05 and 10 wt %, more particularly in the range of about 0.1 and about 7 wt %, still more particularly in the range of about 0.25 and about 5 wt %, for example about 0.5 wt %, about 1 wt %, about 2.5 wt % or about 4 wt %, referred to the total weight of the composition.

Solvents useful for the sake of the present invention are liquids that may be selected from the group comprising
- alcohols, such as ethanol, propanol and isopropanol, and mixtures thereof;
- polyols, such as, 2-ethane diol, 1,2-propane diol, 1,3-propane diol, dipropylene glycol, 1,4-butane diol, glycerol, pentaerythritol (CAS: 115-77-5), 1,4-butane diol, 1,2-butane diol, 1,2-pentane diol, 1,2-hexane diol, 1,2-heptane diol, 1,2-octane diol, and the like;
- glycol ethers and esters, such as dipropylene glycol methyl ether acetate (CAS: 88917-22-0), tripropylene glycol methyl ether (CAS: 25498-49-1), dipropylene glycol methyl ether (CAS: 34590-94-8), dipropylene glycol n-butyl ether (CAS: 29911-28-2), 3-methoxy-3-methyl-1-butanol (CAS: 56539-66-3) and the like;
- isosorbide dimethyl ether (CAS: 5306-85-4), (2,2-dimethyl-1,3-dioxolan-4-yl)methanol (CAS: 100-79-8), and the like;
- mixtures thereof.

In a preferred embodiment, the personal care composition of the invention comprises at least one polyol, wherein the level of at least one polyol in the composition is in the range of 0.5 and 50 wt %, more particularly in the range of about 1 and about 25 wt %, still more particularly in the range of about 2 and about 10 wt %, for example about 2 wt %, about 4 wt % or about 6 wt %, referred to the total weight of the composition.

Oils that are useful for the sake of the present invention are liquids that may be selected from the group comprising
- mineral oils, petrolatum, hydrogenated isoparaffins, hydrogenated polyisobutylene, and silicone oils:
- vegetable and algae oils, such as rapeseed oil, sunflower oil, olive oil, argan oil, apricot oil, jojoba oil, aloe vera oil, ricinus oil, grape seed oils, hydrogenated castor oil, and the like;
- esters, such as isopropyl myristate, methylheptyl isostearate, isononyl isononanoate.

In a preferred embodiment, the personal care composition of the invention comprises at least one oil, which can particularly be an essential oil, wherein the level of the at least one oil in the composition is particularly in the range of 0.5 and 50 wt %, more particularly in the range of about 1 and about 25 wt %, still more particularly in the range of about 2 and about 10 wt %, for example about 2 wt %, about 4 wt % or about 6 wt %, referred to the total weight of the composition.

Preservatives that are particularly useful for the sake of the present invention may be selected from the group comprising benzoic acid and its salts; salicylic acid and its salts; 4-hydroxybenzoic acid and its esters and salts; sorbic acid and its salts, formaldehyde and paraformaldehyde; biphenyl-2-ol and its salts; zinc pyrithione (CAS 13463-41-7); chlorobutanol; formic acid and its salts, dibromohexamidine isethionate (CAS: 93856-83-8); Thiomersal (CAS: 54-64-8); phenylmercuric salts; undec-10-enoic acid and its salts; Hexetidine (CAS: 141-94-6); 5-bromo-5-nitro-1,3-dioxane (CAS: 30007-47-7); 2-bromo-2-nitropropane-1,3-diol (CAS: 52-51-7); dichlorobenzyl alcohol (CAS: 1777-82-8); triclocarban (CAS: 101-20-2); para-chloro-meta-cresol (CAS: 59-50-7); Triclosan (CAS: 3380-34-5); chloroxylenol (CAS: 3380-34-5); imidazolidinyl urea (CAS: 39236-46-9); polyaminopropyl biguanidine (CAS: 32289-58-0/27083-27-8/28757-47-3/133029-32-0); phenoxyethanol (CAS: 122-99-6); methenamine (CAS: 100-97-0); Quaternium-15 (CAS: 4080-31-3); Climbazole (CAS: 38083-17-9); 1,3-bis(hydroxymethyl)-5,5-dimethylimidazolidine-2,4-dione (CAS: 6440-58-0); benzyl alcohol; 1-hydroxy-4-methyl-6-(2,4,4-trimethylpentyl)-2 pyridon and its monoethanolamine salt (CAS: 50650-76-5/68890-66-4); 2,2'-methylenebis(6-bromo-4-chlorophenol) (CAS: 15435-29-7); 4-isopropyl-m-cresol (CAS: 3228-02-2); 5-chloro-2-methyl-isothiazol-3(2H)-one/2-methylisothiazol-3(2H)-one/magnesium chloride/magnesium nitrate mixture (CAS: 26172-55-4, 2682-20-4, 55965-84-9); 2-benzyl-4-chlorophenol (CAS: 120-32-1); 2-chloroacetamide (CAS: 79-07-2); chlorhexidine (CAS: 55-56-1); chlorhexidine digluconate (CAS: 18472-51-0); chlorhexidine dihydrochloride (CAS: 3697-42-5); 1-phenoxypropan-2-ol; alkyl (C12-C22) trimethyl ammonium bromide and chloride (CAS: 17301-53-0/57-09-0/112-02-7/1119-94-4/112-00-5/1120-02-1/112-03-8); 4,4-dimethyl-1,3-oxazolidine (CAS: 51200-87-4); diazolidinyl urea (CAS: 78491-02-8); benzenecarboximidamide, 4,4'-(1,6-hexanediylbis(oxy))bis-?, and its salts (including isothionate and p-hydroxybenzoate) (CAS: 3811-75-4/659-40-5/93841-83-9); glutaraldehyde; 5-ethyl-3,7-dioxa-1-azabicyclo [3.3.0] octane (CAS: 7747-35-5); 3-(p-Chlorophenoxy)-propane-1,2-diol (CAS: 104-29-0); sodium hydroxymethylamino acetate (CAS: 70161-44-3); benzethonium chloride (CAS: 121-54-0); benzalkonium halides and saccharinate (CAS: 8001-54-5/63449-41-2/91080-29-4/68989-01-5/68424-85-1/68391-01-5/61789-71-7/85409-22-9); phenylmethoxy-methanol (CAS: 14548-60-8); 3-iodo-2-propynylbutylcarbamate (CAS: 55406-53-6); 2-methyl-2H-isothiazol-3-one (CAS: 2682-20-4); ethyl lauroyl arginate HCl (CAS: 60372-77-2); citric acid, silver citrate; silver chloride; inorganic sulphites and hydrogensulphites; and mixtures thereof.

In preferred embodiment, the preservative is an Ecocert®-approved preservative selected from the group comprising various blends of sodium benzoate, potassium sorbate, benzyl alcohol, and disodium salt of ethylenediamine tetracetic acid; glyceryl caprylate; para-anisic acid; blends of benzyl alcohol, salicylic acid, glycerol and sorbic acid; combinations of sorbic acid and potassium sorbate, or benzoic acid, potassium benzoate and sodium benzoate; blends of Methylparaben (CAS: 99-76-3), propylparaben (CAS: 94-13-3) and 2-bromo-2-nitropropane-1,3-diol (Bronopol, CAS: 52-51-7); gluconolactone (CAS: 90-80-2) and sodium benzoate; dehydroacetic acid (3-acetyl-2-hydroxy-6-methyl-4H-pyran-4-one; CAS; 520-45-6) and benzyl alcohol; and the like.

In preferred embodiment, the personal care composition of the invention comprises at least one preservative, wherein the level of the at least one preservative in the composition is particularly in the range of 0.0001 and 5 wt %, more particularly in the range of about 0.005 and about 2.5 wt %, still more particularly in the range of about 0.01 and about 1 wt %, for example about 0.05 wt %, about 0.1 wt %, or about 0.5 wt %, referred to the total weight of the composition.

In a particular embodiment, the fibrous material comprising the micro-scaled fibril agglomerates and/or nano-scaled fibril agglomerates, in particular the mixture, the dry mixture or the moistened mixture, is combined with at least one polymer, which may be synthetic or natural, at least one preservative, at least one polyol, and, optionally, an oil. The dry mixture and the moistened mixture are described further below in this document. Compositions according to this particular embodiment are characterized by enhanced sensory properties, such as firm texture, pleasant aspect and improved skin feel.

Other functional ingredients may comprise surfactants selected from the group comprising
- anionic surfactants, for example C10-C22 alkylester sulphonates, such as alpha-sulpho fatty acid methyl esters and ethyl esters; alkyl sulphates, such as sodium dodecyl sulphate; alkyl ether sulphates obtained by ethoxylation of an alkyl alcohol followed by sulphonation using sulphur trioxide; sodium alkyl isethionate; sodium alkoyl sarcosinate, such as sodium dodecanoyl (methyl)aminoacetate; sodium laurylglucosides hydroxypropylsulphonate; potassium laureth phospate;
- cationic surfactants, for example quaternized long chain alkyl ammonium halides, such as distearyldimethylammonium chloride, behenyltrimethylammonium chloride, palmitamidopropyldimethyl-ammonium chloride; linoleamidopropyl ethyldimethyl ammonium ethylsulphate, lecithin and lysolecithin;
- cationogenic surfactants, for example fatty amines, such as lauriminopropyldimethyl amine, tridecyl amine, N-oleyl-1,3-propane diamine, and ethoxylated fatty amines, such as ethoxylated N-tallow-1,3-propanediamine;
- zwitterionic surfactants derived from the reaction between compounds having alkyl quaternary ammonium, phosphonium, or sulfonium groups and compounds having carboxyl, sulfonate, sulfate, succinate, phosphate or phosphonate groups, such as for example coco dimethylcarboxymethyl betaine, lauryl dimethyl carboxymethyl betaine, stearyl bis-(2-hydroxyethyl) carboxymethyl betaine; amidoalkyl, sulfoalkyl and alkyl amidosufo betaines, such as cocoamidopropyl betaine, cocodimethylsulfopropyl betaine, lauryl dimethyl sulfoethyl betaine, and lauryl bis-(2-hydroxyethyl) sulfopropyl betaine;
- amphoteric surfactants, for example sodium 3-dodecylimino propionate and sodium 3-dodecyliminopropane sulphonate.
- non-ionic surfactants, for example C4-C22 alkyl ethoxylates with about 1-25 ethylene oxide units; ethoxylated/propoxylated akyl alcohols, such as [C10] deceth-n, laureth-n and trideceth-n, where n is an integer indicating the number average number of ethylene oxide moieties in ethoxyl chain; castor oil ethoxylate, alkyl dialkyl amine oxides; alkanoyl glucose amides; ethoxylated sorbitol alkyl esters, such as sorbitol polyethylene glycol ethers, with 3 to 30 ethoxyl groups, esterified with oleic, myristic, stearic, palmitic acid, and the like; sorbitan alkylate, such as sorbitan palmitate, sorbitan oleate, and the like; polyoxyethylene sorbitan fatty acid esters, such as Polysorbate 20, Polysorbate 60 and Polysorbate 80; C10-C18 alkyl amine oxides and C8-C12 alkoxy ethyl dihydroxy ethyl amine oxides, such as N,N-dihydroxyethyl-N-stearamine oxide, ethoxylated lauramide and lauryldimethyl-amine oxide; cocamide diethanolamine (CAS: 68603-42-9), alkyl polyglycosides, such as glyceryl stearate, sucrose laurate and sucrose palmitate; ethoxylated alkyl glucose dialkyl esters, such as polyethyleneglycol-120 methyl glucose dioleate; mono- and dialkyl polyglycerides, such as octanoic acid hexaglyceryl ester, riccinoleic acid hexaglyceryl ester, cocoic acids tetraglyceryl esters, and caprylic/capric acid triglycerides; ethoxylated hydrogenated castor oil, sorbitan olivate, cetearyl olivate;
- mixtures thereof.

The surfactants listed hereinabove may be admixed with C10-C24 alkyl alcohols, such as cetearyl alcohol, stearyl alcohol and mixtures thereof.

Preferably, the surfactants are water-soluble or water-dispersible.

Other functional ingredients may comprise:
- alpha hydroxy acids, such as glycolic acid, lactic acid, malic acid, citric acid, tartaric acid, and beta-hydroxy acid, such as salicyclic acid (these acids may be partially or fully neutralized in the personal care compositions, which means that both protonated (undissociated) form and unprotonated (dissociated) form may coexist in the composition, wherein the counterion of the unprotonated form is usually sodium, potassium, calcium, and the like; the same remark applies to the salts of these acids; the same remark also applies to the other acids as mentioned hereinunder and in the following and to their salts);
- pyrrolidone carboxylic acid (CAS 149-87-1, CAS 98-79-3);
- anisic acid and its salts;
- dicarboxylic acids, such as sebacic acid, levulinic acid, and their salts;
- proteins and peptides, such as collagen, heptapeptide-8, acetylhexapeptide-3 (CAS: 616204-22-9), acetyloctapeptide-8 (CAS: 868844-74-0), palmitoyl tetrapeptide, palmitoyl pentapeptide (CAS: 214047-00-4), progerin;
- hydrolized soy proteins, hydrolyzed keratin;
- lipides, such as the oils mentioned hereinabove; glycolipides; phospholipides; sphingolipides, such as ceramides; sterols and steroids, such as stigmasterol and β-sitosterol;
- fatty acids and hydroxy fatty acids, and their salts and esters, such as 10-hydroxydecanoic acid, linoleic acid, oleanolic acid, stearic acid, potassium cocoate, potassium oleate, isopropyl palmitate, myristyl acetate;
- fatty alcohols, such as docosanol, 2-octyldodecanol
- glycerine ethoxylate, such as glycereth-26 (CAS: 31694-55-0);
- calcium gluconate (CAS: 299-28-5);
- polidocanol (CAS: 9002-92-0) and polidocanol derivatives;
- urea, allantoin (CAS: 97-59-6), caffein, pyroctone olamine (CAS: 68890-66-4), amino acids and their derivatives, such as L-arginine, ergothionine and alanine, acetyl carnitine hydrocloride (CAS: 5080-50-2), decarboxy carnosine hydrochloride (CAS: 57022-38-5), glucosamine hydochloride (CAS: 66-84-2);
- alpha-lipoic acid (CAS: 1077-28-7);
- alkaline base, such triethanolamin and sodium hydroxyde;
- flavonoids and isoflavonoids, such as epicatecine and epicatechin gallate, epigallocatecin and epigallocatecin, pigenin, juteolin, quercetin, apiin, isorhamnetin, patuletin, genistein, glabrindin, soy isoflavones, and catechins;
- polyphenols, such as resveratrol, tetrahydrobisdemethoxycurcumin (CAS: 113482-94-3);
- anti-oxydants, such as butylated hydroxy toluene; pentaerythryl tetra-di-t-butyl hydroxycinamate
- anthocyanins, such as aurantinidin, cyanidine, elphinidine, europinidin, pelargonidin, malvidin, peonidin, petunidin and rosinidin;
- hydroxyphenyl propamidobenzoic acid (CAS: 697235-49-7);

- minerals, such as titanium oxide, kaolin, mica, iron oxides, zinc, zinc oxide, tin oxide, calcium sodium borosilicate, mica, isopropyl titanium triisostearate (CAS: 61417-49-0);
- organic dyes and pigments, such as Yellow 5 (Tartrazine, CAS: 1934-21-0), Red 33 (disodium 5-amino-4-hydroxy-3-(phenylazo)-naphthalene-2,7-disulfonate; CAS: 3567-66-6);
- vitamins and vitamin derivatives, such as panthenol, tocopherol and tocopheryl acetate, dilauryl citrate, ascorbic acid, niacinamide, sodium ascorbyl phosphate, tetrahexyldecyl ascorbate, retinol, retinyl palmitate, panthenol (Vitamine B, CAS 81-13-0);
- terpenes, including their derivatives, such as menthol, menthyl lactate, ethyl menthane carboxamide, limonene, eucalyptol, cineol, camphor, borneol;
- sesquiterpenes and triterpenes, including their derivatives, such as bisabolol, glycyrrhetinic acic and its salts and esters, saponins, glycyrrhetic acid and its salts and esters, stearyl glycyrrhetinate, glycyrrhizinic acid and its salts and esters, phytosterol;
- ubiquinones;
- aromatic hydrocarbons, such as azulene;
- sequestring ingredients, such as tetrasodium glutamate triacetate, sodium phytate (CAS: 14306-25-3/34367-89-0), ethylene diamine tetracetic acid and salts thereof;
- organic UV-absorbing ingredients, such as 1-(4-Methoxyphenyl)-3-(4-tert-butylphenyl)propane-1,3-dione (CAS: 70356-09-1), butyl methoxydibenzoylmethane (CAS: 274-581-6), ethylhexyl salicylate (CAS: 118-60-5), ethylhexyl methoxycinnamate (CAS: 5466-77-3), 3,3,5-Trimethylcyclohexyl 2-hydroxybenzoate (CAS: 118-56-9), ethylhexyl methoxycrylene (CAS: 947753-66-4), Drometrizole trisiloxane (CAS: 155633-54-8), (2-hydroxy-4-methoxyphenyl)-(phenyl)methanone (CAS: 131-57-7), benzophenone;
- whitening ingredients, such as kojic acid (5-hydroxy-2-(hydroxymethyl)-4H-pyran-4-one, CAS: 501-30-4), hydroquinone;
- waxes and butters, such as bees wax, Ozokerite, Candelilla wax, Carnauba wax, Shea butter, Shorea Stenoptera seed butter, Cocoa seed butter, Astrocaryum murumuru seed butter;
- carbohydrates and sugar alcohols, and their derivatives, such as ribose; arbutin (CAS: 497-76-7), erythrulose, isomerized saccharides, sorbitol;
- deodorizing ingredients, such as ethylhexyl glycerins, zinc ricinoleate, aluminium chlorohydrate, aluminium zirconium tetrahydrochlorex glycine (CAS: 134910-86-4);
- particulates, such as grinded nut and seed shells, such as Macadamia shell powder and Almond shell powder, silicates, calcium carbonate, Nylon-6 and Nylon-12 beads, polyethylene beads, polytetrafluoroethylene beads, polylactic acid beads, glycol montanate beads, high-melting point waxes, Carnauba wax, rice bran wax, micro-crystalline cellulose, Oatmeal;
- plant extracts, juices and essential oils from, Acacia farnesiana, Acai, Ahnfeltia, Ahnfeltia concinna, Alaria esculenta, Aleurites moluccana seed, alfalfa extract, algae, bitter Almond, Aloe leaf, Aloe vera, Alteromonas ferment, Althaea rosea, Althea officinalis, Anacystis nidulans, Ananas sativus, Andiroba, Amica, Angelica root, Annato, Apple, Apricot kernel, Arachis hypogaea extract, Arctium, Arctostaphylos uva ursi leaf, Arjuna, Arnica, Artemia, Artemisia, Ascophyllum nodosum, Asparagopsis armata, Astragala, Atractyloydes lancea root, Avena sativa, Awapuhi, Babassu, bakuchiol, Bala, bamboo shot, Banana, Bark tree, Barley grass, Beet, Benzoin, Berberis aristata, Bergamot, Bertholletia excelsa, Beta vulgaris root, Betula alba, Bilberry, Birch bark, Birch leaf, black Cohosh, Blackcurrant, black Elderberry, black Loccust, black Mulberry, black Pepper, black Raspberry, black Snakeroot, black tea, Blackberry, Bladderwrack, blue Vervain, Boerhavia diffusa root, Borago seed, Bugbane, Bupleurum, Burdock, butcher's broom, Calendula, Calluna vulgaris flower, Camphor, Cayenne, Centaurea cyanus, Centella asiatica, Chamomile, Chrysanthemum, Cinnamon bark, Cocash weed, Coriander, Corn flower, Cornus, Coughweed, Cranberry seed, Curcumin, Cypress, Dandelion, Dogwood, Echinacea, Elder flower, Epilobium angustifolium, Eucalyptus, Evodia rutaecarpa, Fennel, Feverfew, Filipendula rubra, Fireweed, Flaxseed, Fu Ling, Gentiana, Geranium, Ginger root, Ginkgo, Ginseng, Gotu kola, grape seed extract, green tea, Gromwell, Honey, Honeysuckle flower, Horse chestnut, Ilex paraguariensis, Jasmine, Juniper, Jujube, Haw, Hawthorne, Helianthus, Jasmine, Kava kava, Kawa, Laminaria ochroleuca, Lamium album flower, Lappa, Lavender, Leontopodium alpinum, Lemon, Lemon peel, Lemon grass, Licorice, Life root, Lime tree, Lin, Linden flowers, Lithospermum erythrorhizon, Lonicera, Lotus seed, Mallow, Marshmallow, Marigold, Marjoram, Mate, Meadow sweet, Morinda citrifolia, Nettle leaf, Niaouli, Noni, Oat bran, Oat kernel, Oat straw, Oenothera biennis, Orange, Orange blossom, Passion flower, Peru balsam, Pine, Pineapple, Primrose, Pancy, Panish sage, Perilla, Persicaria hydropiper, Phyllanthus emblica fruit, Physalis, Pseudopterogorgia elisabethae, Picea abies, Poria cocos, Portulaca oleracea extract, Propolis, Prunella vulgaris, Ragwort, red Clover, Roman chamomile, rose, Rosmary, Salici, Salix alba bark, Sapindus mukurossi peel, Scutellaria baicalensis, See whip, Senecio, Skullcap, Slippery elm bark, Soap berry, Spiraea ulmaria, Spruce, Squaw root, Squaw weed, St. John's wort, Tamanu, Tea tree, Thyme, Turmeric, Ulva lactuca, Uncaria tomentosa, Vaccinium macrocarpon fruit, Valerian root, Vanilla planifolia fruit, Violet, White birch, Wild yam, Wintergreen, Witch hazel, Wormwood, Yarow, Yerba mate, Ylang Ylang, Yohimbe, Yucca; and/or
- fragrances, such as terpene alcohols and esters, cycloalkyl esters and ketones, alkyl and aromatic aldehydes, oxides, ketals, and the like.

Other functional ingredients may be found in the list of International Nomenclature of Cosmetic Ingredients (INCI) of the Personal Care Products Council, available for example at http://www.makingcosmetics.com/articles/INCI-list.pdf, or in the International Nomenclature of Cosmetic Ingredients Handbook, 16$^{th}$ edition, J. Nikitakis and B. Lange (editors), Personal Care Products Council, 2016, ISBN 1-882621-55-7.

The personal care composition according to the invention may also comprise any topical pharmaceutical ingredient for human and veterinary use that is soluble or suspendable in the composition. Suitable pharmaceutical ingredients include, but are not limited to:
- antihistamines such as diphenhydramine HCl, tripelennamine and pyrilamine maleate, diphenhydramine hydrochloride and chlorpheniramine maleate;
- corticosteroids, such as hydrocortisone, dexamethasone, flumethasone, prednisolone, methylprednisolone, clobetasol propionate, betamethasone benzoate, betamethasone dipropionate, diflorasone diacetate, fluocinonide, mometasone furoate, and triamcinolone acetonide;

anti-inflammatory ingredients, such as carprofen, diclofenac, diflunisal, etodolac, fenoprofen, flufenamic acid, fluocinolone acetonide, flurbiprofen, ibuprofen, indomethacin, ketorolac, meclofenamate, mefenamic acid, nabumetone, naproxen, oxaprozin, oxyphenbutazone, phenylbutazone, piroxicam, meloxicam, pirprofen, salsalate, sulindac, tenoxicam, tiaprofenic acid, tolmetin, triamcinolone acetonidebetamethasone valerate, celecoxib, fluocinonide, hydrocortisone, and sodium salicylate, etofenamat, heparin;

antibiotics, such as penicillins, tetracyclines, cephalosporins, quinolones, lincomycins, macrolides, sulfonamides, glycopeptides, aminoglycosides, arbapenems;

antimicrobial or bacteriostatic ingredients, such as neomycin, gentamycin, polymyxin and clindamycin, benzoxonium chloride;

antifungals such as miconazole nitrate, clotrimazole, nystatin and haloprogin;

anesthetic ingredients lidocaine, dibucaine, benzocaine and pramoxine HCl, prilocaine;

analgesic ingredients, such as glycol salicylate, methyl salicylate, 1-menthol, d,l-camphor and capsaicin; and/or steroids and triterpenes, such as anabolic steroid, androgenic steroid, corticosteroid, glucocorticoid, gonadotropin, human growth hormone, progesterone, progestogen, and progestogen and estrogen, enoxolone;

According to a preferred embodiment of the invention, the personal care composition, which in this case is preferably a gel, a gel mask or a sorbet mask, comprises a.) 0.1 to 30 wt %, preferably 0.5 to 20 wt %, more preferably 1 to 10 wt %, of the fibrous material comprising the micro-scaled and/or nano-scaled fibril agglomerates, referred to the total weight of the composition;

b.) up to 25 wt %, preferably up to 10 wt %, of one or more polyols referred to the total weight of the composition;

c.) up to 5 wt %, preferably 0.005 to 2.5 wt %, of one or more preservatives, referred to the total weight of the composition;

d.) one or more functional ingredients being different from the one or more polyols mentioned under b.) and different from the one or more preservatives mentioned under c.); and e.) water, which is preferably deionized water, and which advantageously completes the composition to 100 wt %.

In a particular embodiment, the personal care composition of the invention is a self-standing gel having a homogeneous, translucent and aqueous aspect and providing a cool and slightly wet feel on the skin absorption, and which may be applied as a mask, for example a facial mask. Gel masks according to this particular embodiment are well suited for the topical delivery of functional cosmetic ingredients mentioned hereinabove to the skin and are useful as a delivery system for ingredients and compositions for the treatment and regulation of topical disorders of facial area skin, such as excess fat reduction, venous insufficiency, stretch marks, rosacea, acne, pimples, skin redness, wrinkles, varicose veins, cellulite, age-spots, skin aging, and the like. The gel mask may also comprise exfoliating ingredients and particulate materials and used as scrub. Alternatively, the gel mask may have the aspect of a sorbet having an inhomogeneous, finely bumpy texture, translucent aspect. The level of fibrous material comprising micro-scaled and/or nano-scaled fibril agglomerates in the gel mask or a sorbet mask is preferably in the range of 0.1 to 35 wt %, for example 0.5 wt %, 1 wt %, 1.5 wt %, 5 wt %, 10 wt %, 20 wt % or 30 wt % referred to the total weight of the gel mask or the sorbet mask.

In a specific embodiment, the gel mask or sorbet mask comprises:

a) 0.1 to 30 wt %, preferably 0.5 to 20 wt %, more preferably 1 to 10 wt %, of the fibrous material comprising micro-scaled and/or nano-scaled fibril agglomerates referred to the total weight of the gel mask or sorbet mask;

b) Up to 25 wt %, preferably up to 10 wt %, of a one or more polyols referred to the total weight of the gel mask or sorbet mask;

c) 0.0001 to 5 wt %, preferably about 0.005 to about 2.5 wt %, of one or more preservative referred to the total weight of the gel mask or sorbet mask;

d) One or more functional cosmetic ingredients, preferably selected from but not limited to the groups mentioned in this document, and being different from the one or more polyols mentioned under b) and different from the one or more preservatives mentioned under c);

e) Water completes the gel mask or sorbet mask to 100 wt %.

In a particular embodiment, the personal care composition of the invention is a cream-gel having a homogeneous, translucent milky aspect, and providing a cool and silky feel on the skin, and a fast absorption into the skin under application. Such a cream-gel may be used as topical formulation of the delivery of cosmetic ingredients and compositions for various treatments, as depicted in this document. The level of fibrous material comprising micro-scaled and/or nano-scaled fibril agglomerates in the cream-gel is preferably in the range of 0.1 to 10 wt %, for example 0.25 wt %, 0.5 wt %, 1 wt %, 2.5 wt %, 5 wt % or 7.5 wt %, referred to the total weight of the cream-gel.

In the context of the present invention, the term "translucent milky" is used to describe a material that is substantially opaque but still permits some light to pass through thin portions of it, for example close to the surface or when applied in layers. The translucent milky aspect is also referred to "opalescent" or "pearlescent".

According to another preferred embodiment of the invention, the personal care composition, which in this case is preferably a cream-gel or a serum, comprises a.) 0.1 to 10 wt %, preferably 0.5 to 10 wt %, more preferably 1 to 5 wt %, of the fibrous material comprising the micro-scaled and/or nano-scaled fibril agglomerates, referred to the total weight of the composition;

b.) up to 25 wt %, preferably up to 10 wt %, of one or more polyols referred to the total weight of the composition;

c.) up to 5 wt %, preferably 0.005 to 2.5 wt %, of one or more preservatives referred to the total weight of the composition;

d.) one or more functional ingredients being different from the one or more polyols mentioned under b.) and different from the one or more preservatives mentioned under c); and e.) water, which is preferably deionized water, and which advantageously completes the composition to 100 wt %.

In a particular embodiment, the personal care composition of the invention is a cream-gel having a transparent to translucent to milky aspect at rest and becoming transparent under application on skin.

In a particular embodiment, the personal care composition of the invention is a minimalist formulation consisting of:

a) The fibrous material comprising micro-scaled and/or nano-scaled fibril agglomerates; and
b) optionally a preservative; and
c) not more than 11 functional ingredients, preferably not more than 9 functional ingredients, more preferably not more than 7 functional ingredients, even more preferably not more than 5 functional ingredients selected from the group comprising synthetic and natural polymers, polyols, solvents, mineral and vegetal oils, surfactants, fatty acid and fatty alcohol esters, C10-C24 fatty acids and their salts, C10-C24 fatty alcohols, alpha and beta hydroxy acids and their salts, salicyclic acid and its salts, dicarboxylic acids and their salts, pyrrolidone carboxylic acid, proteins and peptides, collagen, glycolipides; phospholipides; sphingolipides, sterols and steroids, glycerine ethoxylate, calcium glyconate, polidocanol, urea, allantoin, caffein, pyroctone olamine, acetyl carnitine, amino acids and their derivatives, quaternary amines, alpha-lipoic acid, alkaline base, flavonoids and isoflavonoids, polyphenols, anthocyanins, minerals, organic dyes and pigments, vitamins and their derivatives, terpenes and their derivatives, sesquiterpenes and their derivatives, triterpenes and their derivatives, ubiquinones, sequestering ingredients, UV-absorbing ingredients, antioxidants, waxes and butters, carbohydrates and sugar alcohols, and their derivatives, deodorizing ingredients, mineral and vegetal particulates, plant extracts, juices, essential oils and fragrances; and
d) water.

According to a another preferred embodiment of the invention, the personal care composition comprises
a) one or more preservatives; and
b) not more than 11 functional ingredients, preferably not more than 9 functional ingredients, more preferably not more than 7 functional ingredients, even more preferably not more than 5 functional ingredients selected from the group comprising synthetic and natural polymers, solvents, mineral and vegetal oils, surfactants, fatty acid and fatty alcohol esters, C10-C24 fatty acids and their salts, C10-C24 fatty alcohols, alpha and beta hydroxy acids and their salts, salicyclic acid and its salts, dicarboxylic acids and their salts, pyrrolidone carboxylic acid, proteins and peptides, collagen, glycolipides; phospholipides; sphingolipides, sterols and steroids, glycerine ethoxylate, calcium glyconate, polidocanol, urea, allantoin, caffein, pyroctone olamine, acetyl carnitine, amino acids and their derivatives, quaternary amines, alpha-lipoic acid, alkaline base, flavonoids and isoflavonoids, polyphenols, anthocyanins, minerals, organic dyes and pigments, vitamins and their derivatives, terpenes and their derivatives, sesquiterpenes and their derivatives, triterpenes and their derivatives, ubiquinones, sequestering ingredients, UV-absorbing ingredients, antioxidants, waxes and butters, carbohydrates and sugar alcohols, and their derivatives, deodorizing ingredients, mineral and vegetal particulates, biological preservatives, plant extracts, juices, essential oils and fragrances; and
c) water, which is preferably deionized water.

In the context of the present invention, the sensory features of the personal care composition can be assessed by panelists, for example by subjectively answering a sensory testing inquiry form, according to methods known to the art (see for example Peter Busch, Thomas Gassenmeier, "Evaluation of Cosmetics by Sensory Assessment", in "Cutaneous Biometrics", D. A. Schwindt and H. I. Maibach (Edts), Springer, 2000, pages 65-80).

The current invention also relates to a method to produce the personal care composition as indicated above. The method comprises at least the steps of
a.) comminuting dry pulp by mechanical means;
b.) dispersing said comminuted dry pulp in a liquid; and
c.) further comminuting the pulp dispersed in the liquid to form a mixture of a fibrous material comprising micro-scaled and/or nano-scaled fibril agglomerates and the liquid, wherein the further comminuting preferably is performed by means of a mineral material, wherein the mixture preferably is substantially free, more preferably completely free, of visible isolated fibrils.

The method preferably comprises the additional step of:
d.) adding at least one functional ingredient to the mixture.

The method mentioned above allows to produce personal care compositions which are substantially free of visible isolated fibrils, in particular completely free of visible isolated fibrils. These personal care compositions are particularly well structured and non-irritant and have good drying properties.

In particular the mixture can be used as a basis material for formulating personal care compositions in general, in particular the personal care composition according to the invention. This is in particular the case if the liquid of the mixture comprises water, in particular if the liquid is water.

In order to produce a personal care composition, in particular the personal care composition according to the invention, it is particularly preferred to use the mixture of a liquid, which preferably comprises water, which more preferably is water, and the fibrous material comprising micro-scaled and/or nano-scaled fibril agglomerates, wherein the mixture preferably is substantially free of visible isolated fibrils, more preferably is completely free of visible isolated fibrils. Personal care compositions produced on the basis of such mixtures are particularly well structured and non-irritant and have good drying properties.

The pulp of step a.) is regarded to be dry, if it has a water content that is normal for the corresponding type of pulp, i.e. there are no substantial additions of water or any other liquid. Small additions of water or of another liquid can be present, as long as they do not substantially influence the total weight of the pulp material, i.e. preferably by not more than 15 wt %, more preferably by not more than 10 wt %, even more preferably by not more than 5 wt %. The pulp material is particularly not regarded to be dry in cases, in which it is dispersed in a liquid. The dry pulp preferably comprises at the maximum 15 wt %, more preferably at the maximum 10 wt %, even more preferably 1-9 wt %, most preferably 5 wt % to 8 wt % of water, referred to the total weight of the dry pulp, wherein the water content is measured preferably by means of the standard EN 20638, September 1993.

Preferably, the step a.) is performed without the addition of liquid, i.e. the dry pulp, in particular the dried pulp sheet or the flash-dried pulp, is comminuted without the addition of a liquid.

In a preferred embodiment, the mixture comprises fibrous material comprising micro-scaled and/or nano-scaled fibril agglomerates, wherein the level of the fibrous material in the mixture is in the range from 0.1 to 40 wt %, preferably in the range from 1 to 30 wt %, more preferably in the range from 1 to 20 wt %, even more preferably in the range from 2 to 10 wt %, referred to the total weight of the mixture.

The fibrous material comprising the micro-scaled fibril agglomerates and/or nano-scaled fibril agglomerates is preferably made from plants, more particularly from the pulp of plants, still more particularly from the pulp of wood, still more particularly from the pulp of hardwood, still more particularly from the pulp of the Eucalyptus tree, in particular from the pulp of the Eucalyptus Urograndis tree, and/or from the pulp of the beech tree.

In a preferred embodiment, the fibrous material comprising the micro-scaled fibril agglomerates and/or nano-scaled fibril agglomerates is preferably obtained from the pulp of hardwood, wherein the fibrous material contains low levels of lignin, for example less than 2 wt % referred to the total weight of the fibrous material or less than 1 wt % of lignin referred to the total weight of the fibrous material and/or preferably more than about 10 wt % of xylose, more preferably more than 15 wt % of xylose, referred to the total weight of the dry fibrous material. The amount of xylose comprised by the fibrous material is preferably measured by the information provided by «T. Wolfinger, Dreidimensionale Strukturanalyse and Modellierung des Kraft-Dehnungsverhaltens von Fasergefügen, TU Dresden, Fakultät Umweltwissenschaften, Dissertation submitted in November 2016».

The level of lignin of the fibrous material may be assessed by methods known to the art, such as, for example the method according to the standard TAPPI T222 om-02 of Jun. 16, 2006, which is incorporated herein by reference.

The liquid used for dispersing the dry pulp preferably has a boiling temperature at normal pressure (101325 Pascal) of less than 100° C., more preferably a boiling temperature at normal pressure (101325 Pascal) in the range of 50 to less than 100° C., even more preferably in the range of 50° C. to 90° C. The boiling temperature of less than 100° C. provides the advantage that the liquid can be removed from the fibrous material without damaging the micro-scaled and/or nano-scaled fibril agglomerates. The boiling point of at least 50° C. provides the advantage that the danger of ignition of the liquid is reduced.

According to a preferred embodiment, the liquid is acetone, hexane, cyclohexane, Freon-11, dioxane, t-butyl methyl ether, dimethoxymethane, chloroform, dichloromethane, ethyl acetate, tetrahydrofuran, 2-butanone, 1,2-dimethoxyethane, acetonitrile, and mixture thereof, or a non-aqueous protic solvent, such as ethanol, or isopropanol, or an azeotropic mixture. The use of such liquids to produce the mixture provides the advantage that the mixture can be further used to manufacture the personal care composition.

According to another preferred embodiment, the liquid is an aprotic liquid or a protic liquid, preferably a protic liquid.

Protic liquids that are useful for the sake of the present invention may be selected from the group comprising water, ethanol, isopropanol, 1,2-propanediol, 1,3-propanediol, dipropylene glycol, glycerol, pentaerythritol (CAS: 115-77-5), and mixture thereof. Preferably the protic liquid comprises water. More preferably the protic liquid is water.

Due to the fact that the state of the micro-scaled and/or nano-scaled fibril agglomerates is insensitive to small amounts of ions in water, both deionized and tap water can be used to produce the dispersion comprising the micro-scaled and/or nano-scaled fibril agglomerates for use in personal care composition, although, for cosmetic uses, deionized or distilled water is preferred.

However, water-free liquids may also be preferred for certain product formats, such as balms, primers, deodorant sticks, lip sticks, and the like.

In a further step, the mixture is preferably dried in order to form a dry mixture comprising the fibrous material comprising the micro-scaled and/or nano-scaled fibril agglomerates. The dry mixture comprises a solids content preferably in the range of 70 wt % to 100 wt %, more preferably in the range of 80 wt % to 97 wt %, even more preferably in the range of 85 wt % to 95 wt %, referred to the total weight of the dry mixture. The liquid content, in particular the water content, of the dry mixture preferably is determined by means of standard EN 20638 of September 1993. The dry mixture is preferably in powder form. Furthermore, the dry mixture is preferably substantially free, more preferably completely free, of visible isolated fibrils.

According to a preferred embodiment, the dry mixture is further used as such to produce the personal care composition. According to another preferred embodiment, a liquid is added to the dry mixture again in order to form a moistened mixture. The liquid can be the same or another liquid as the one used for dispersing the dry pulp. In order to disperse the dry mixture in the liquid, preferably a low shear mixer, such as a paddle mixer or a propeller mixer, is used, meaning the dry mixture is dispersed without the use of high shear mixing equipment, such as saw tooth dissolver, rotor-stator homogenizer or high-pressure homogenizer. According to another preferred embodiment, the moistened mixture is further used to produce the personal care composition.

The dry mixture as well as the moistened mixture allow to produce personal care compositions which are well structured and non-irritant with good drying properties.

If the dry mixture or the moistened mixture is substantially free of visible isolated fibrils, in particular completely free of visible isolated fibrils, such a mixture allows to produce a personal care composition which is particularly well structured and non-irritant with good drying properties.

In a preferred embodiment, the mixture comprises up to 5 wt % of a preservative referred to the total weight of the mixture.

The mixture is preferably a dispersion, more preferably an aqueous dispersion. The aqueous dispersion is usually translucent, owing to the presence of light-diffusing micro-scaled and/or nano-scaled fibril agglomerates.

In the context of the present invention, the term "translucent" is used to describe a material permitting light to pass through but diffusing it so that objects disposed on one side of the material are not clearly visible on the opposite side.

Preferably, the personal care composition is prepared by further using the mixture, the dry mixture or the moistened mixture, as a basis material, wherein all other ingredients of the personal care composition to be produced are admixed to the mixture, to the dry mixture or to the moistened mixture.

According to a preferred embodiment, the personal care compositions is produced by further adding at least one functional ingredient, in particular any of the functional ingredients mentioned in this document, to the mixture, to the dry mixture or to the moistened mixture under mild conditions of temperature, preferably room temperature, and without the need of rotor-stator or high-pressure homogenization means.

In a preferred embodiment, the selected functional ingredients are added sequentially to the mixture comprising the liquid and the fibrous material comprising the micro-scaled fibril agglomerates and/or nano-scaled fibril agglomerates, to the dry mixture or to the moistened mixture.

In a particular embodiment, the sequential addition of the functional ingredients into the mixture comprising the fibrous material comprising micro-scaled fibril agglomerates and/or nano-fibril agglomerates and a liquid, wherein the liquid preferably comprises water, into the dry mixture or into the moistened mixture, is achieved by preferably performing the steps in the order of:

1) If required, adding the polyol to the mixture, to the dry mixture or to the moistened mixture under gentle agitation;
2) Adding the preservative to one of said mixtures of the preceding step under gentle agitation;
3) If required, adding the hydrophilic polymer(s) and/or the water-soluble or water-dispersible surfactant(s) under gentle agitation to the mixture of the preceding step until said polymer(s) and/or surfactant(s) are homogeneously dispersed in the mixture
4) If required, adding the oil(s) and/or other hydrophobic ingredients to the mixture of the preceding step and dispersing said oil(s) and/or hydrophobic ingredients by using dissolver or disperser, until a homogeneous pre-emulsion is obtained;
5) If required, adding demineralized water to the mixture of the preceding step under gentle agitation until the desired product consistency is obtained;
6) If required, adding the fragrance to any of the preceding mixtures.

The method mentioned hereinabove differentiates from the state of the art in that at no instance a high pressure or roto-stator homogenization means is required to disperse the functional ingredients in the mixture, the dry mixture or the moistened mixture.

It will be easily understood by the person skilled in the art that some freedom exists as to the way a multitude of different functional ingredients may be formulated in the mixture, the dry mixture or the moistened mixture to provide the personal care compositions according to the invention.

Accordingly, the person skilled in the art, based on experimental trials and applying methods known to the art, will be able to draw the best procedure for each composition falling within the scope of the present invention. For example, the water-soluble or water-dispersible ingredients may be added before or after the hydrophobic ingredients are added, although, preferably, the hydrophilic ingredients are added prior to the addition of the hydrophobic ingredients. Solid water-soluble or water-dispersible ingredients are preferably added prior to the addition of the hydrophobic ingredients. The ingredients that are soluble or dispersible in an apolar medium are preferably admixed with the hydrophobic ingredients or added after these hydrophobic ingredients have been added.

It will also be easily understood by the person skilled in the art that if the mixture, the dry mixture or the moistened mixture comprises a liquid, which does not contain any water, different functional ingredients may be required and the way to incorporate these ingredients into the mixture, the dry mixture or the moistened mixture may also be different in comparison the a mixture, a dry mixture or a moistened mixture comprising a liquid comprising water.

It will also be easily understood by the person skilled in the art, that the personal care compositions according to the invention may be used in various cosmetic and personal care applications, such as cleansing, moisturizing, relaxing/soothing, repairing, filling, conditioning, rejuvenating, decorating, as well as various formats and products, comprising creams, such as skin repair creams, anti-wrinkle creams; serums; body milks; in-shower body lotions; cream-gel, such as hydrating cream-gels, soothing gels, cool revival gels; gel masks, such as face mask; sorbets; soufflés; jellies; mousses; gel-to-water products; cream-to-water products; massage emulsions; elixirs; scrubs; water-based decoration products, such as water-based mascara and blur, concealers; facial and body cleansing gels; shampoos; hair conditioners; styling product, hair replacer, bath and shower gels; sprayable lotions, such as sunscreen lotions; deodorizing compositions; antiperspirants, and the like.

It will be also easily understood by the skilled in the art person that the possible level of any functional cosmetic ingredient in the above personal care compositions will depend on the nature of the functional ingredient, on the magnitude of the desired benefit provided by this ingredient, on formulation-dependent factors such as solubility and mutual compatibility, as well as on external factors, such as price and regulatory provisions.

SHORT DESCRIPTION OF THE FIGURES

Figure 2:
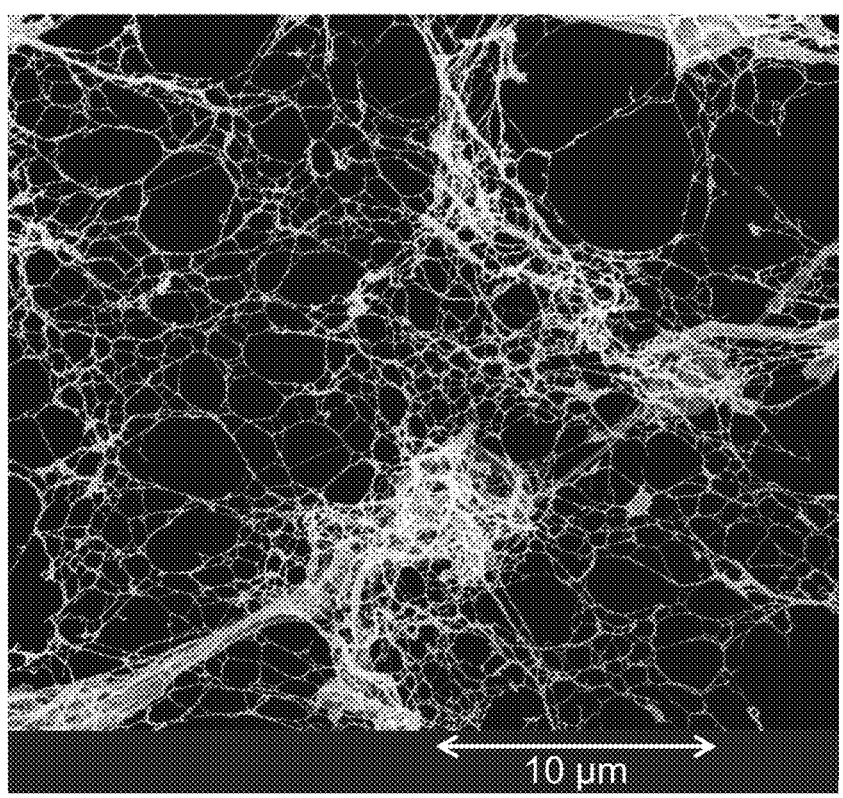
Figure 3:
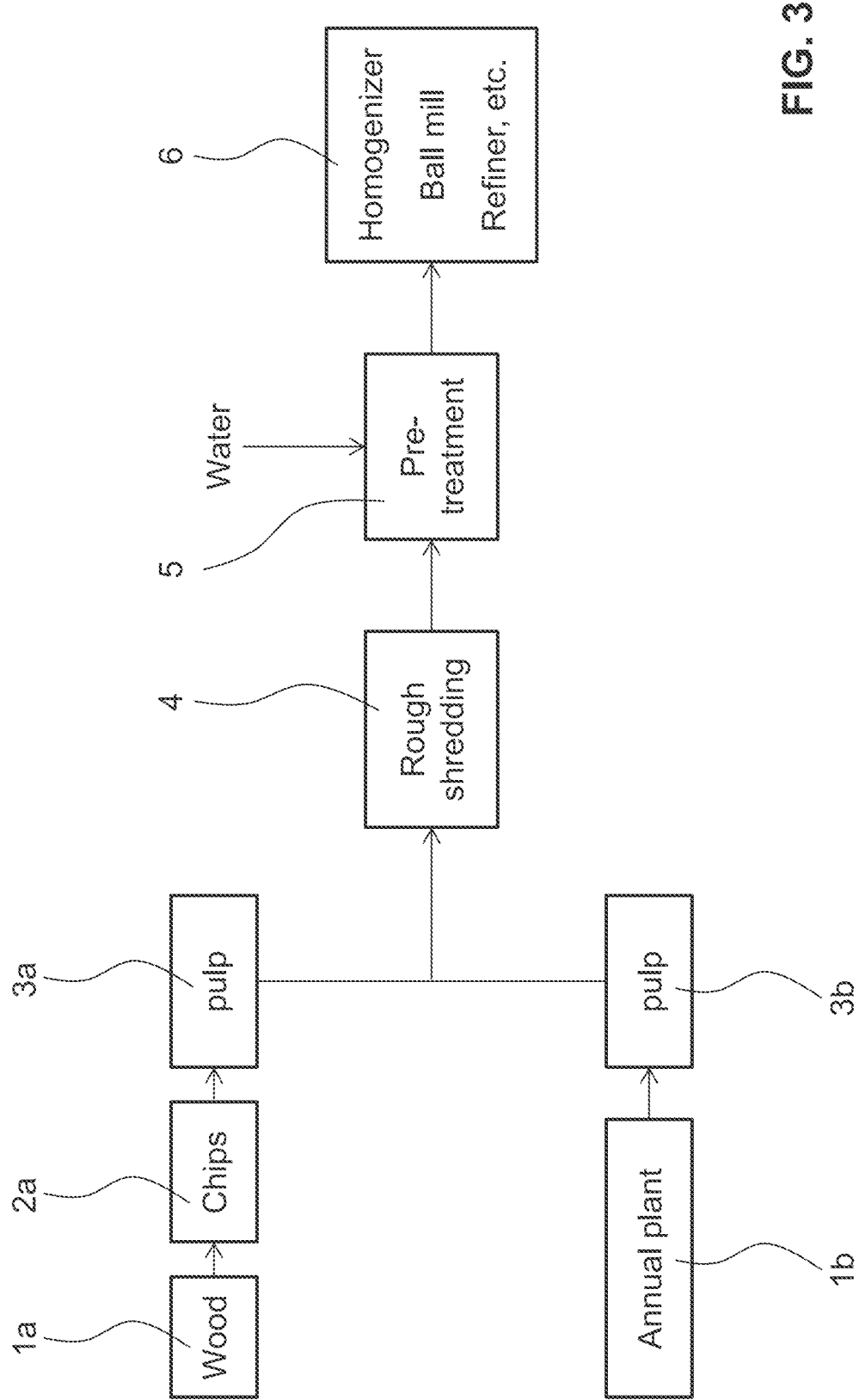
Figure 4:
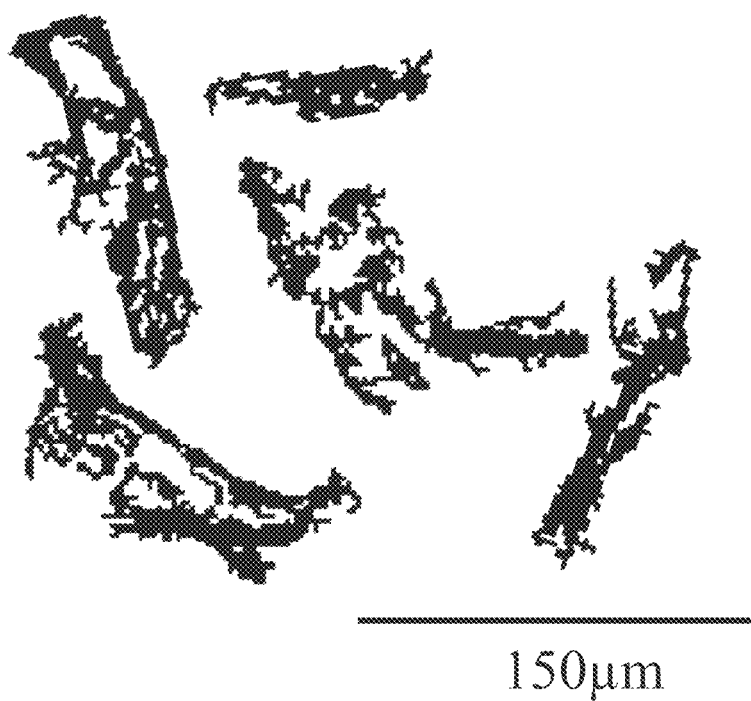
Figure 5:
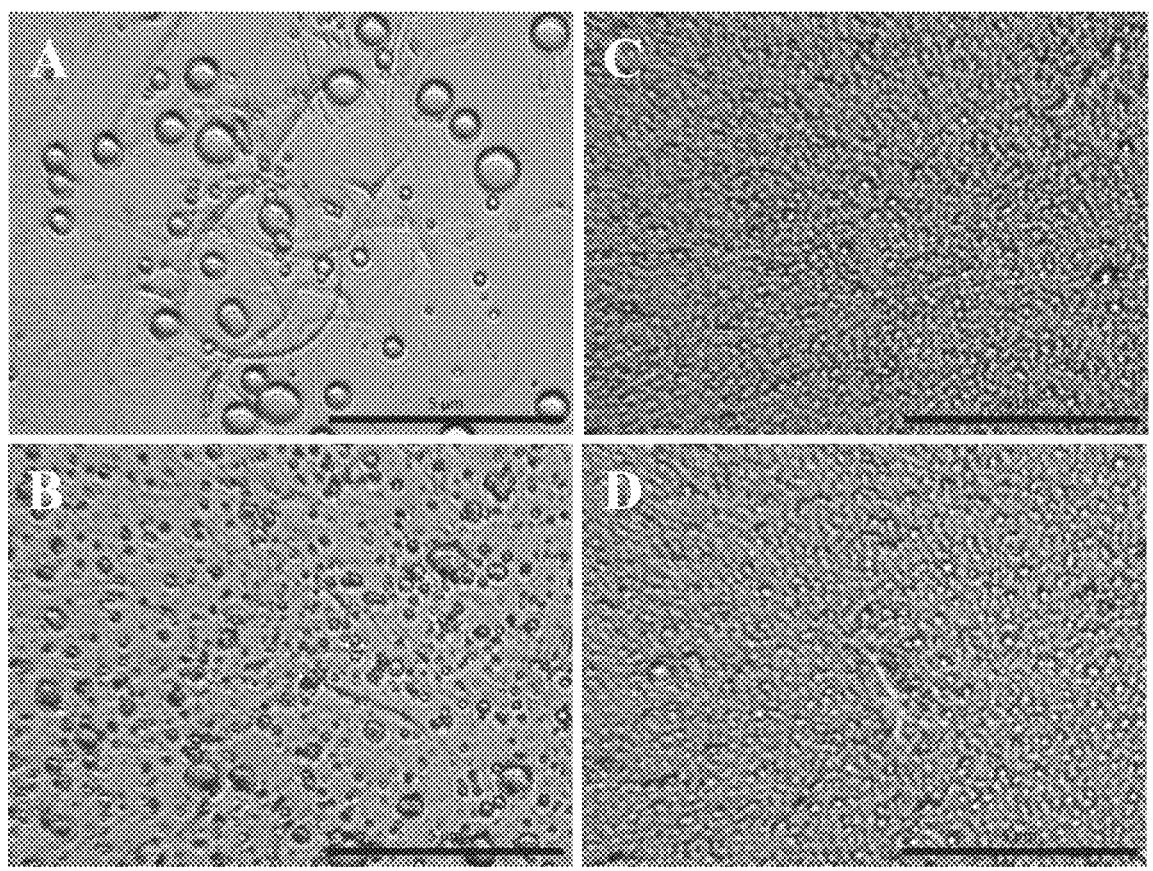
Figure 6:
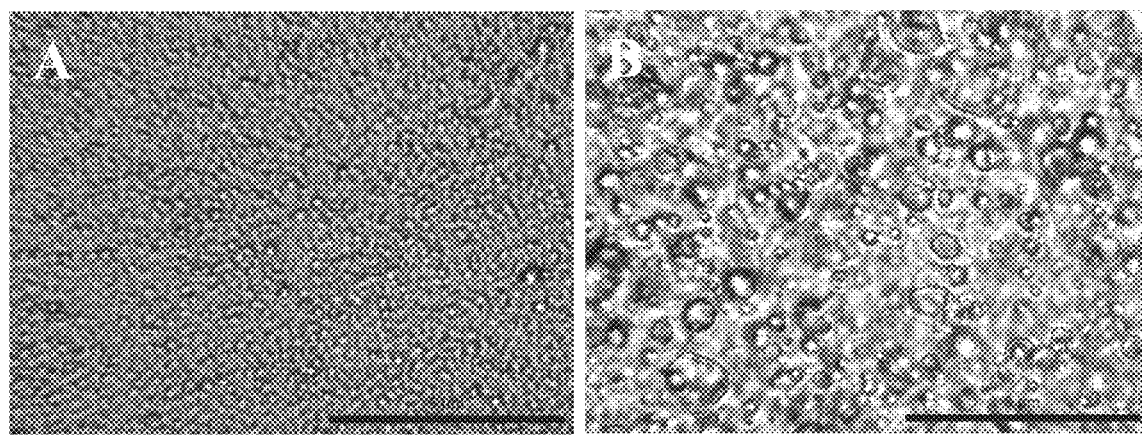

Preferred embodiments of the invention are described in the following with reference to the drawings and to examples, which only serve for illustration purposes, but have no limiting effects. In the drawings it is shown:

FIG. 1 a view of isolated microfibrils, obtained by means of an electron microscope at a magnification of 10'000;

FIG. 2 a view of a part of a micro-scaled fibril agglomerate which is free of visible isolated fibrils, obtained by means of an electron microscope at a magnification of 10'000;

FIG. 3 a flow chart depicting a method to produce an inventive personal care composition FIG. 4 several examples of micro-scaled fibril agglomerates comprised by a fibrous material which is comprised by the personal care composition according to the present invention;

FIG. 5 microscopic images of a composition with microfibrillated cellulose containing no xylose (A) and different xylose contents (B-D); and FIG. 6 microscopic images of the composition of FIG. 5C compared to a composition comprising microcrystalline cellulose.

FIG. 3 shows a flow chart in which method steps of an inventive method for producing a personal care composition are illustrated.

A cellulose-containing material selected from wood 1a or annual plant 1b, or a combination thereof are processed to pulp 3a or 3b according to a conventional method known to the skilled person. The pulp 3a, 3b is preferably in the form of pulp plates or by flash-dried pulp. If wood is used, preferably the Eucalyptus tree, in particular the Eucalyptus Urograndis tree, and/or the beech tree is used.

Specifically, the pulp can also be obtained for example from fruits such as citrus fruits or apples, cereals such as wheat or maize, grass or fiber containing vegetables such as peas, pulses or carottes. The person skilled in the art knows how to process a pulp based on these starting substances.

If wood 1a is used as the original cellulose containing material, it is usually first reduced to wood chips 2a and then, e.g. by purely mechanical means or by means of a purely chemical treatment or by means of a combination thereof, to the pulp 3a. Thus, the wood is delignified and frayed, meaning that the fibers are separated from the original wood structure.

Then, a rough comminution 4 of the pulp 3a and/or 3b, which is preferably in the form of pulp plate or flash-dried pulp, referred to as pulp material thereafter, is carried out. In doing so, the pulp material 3a, 3b is preferably comminuted in its dry state, meaning no substantial amount of liquid, preferably no liquid, is added to the pulp material 3a, 3b before or during the rough comminution 4. During step 4, the pulp material 3a, 3b can for example have a water content of about 5 to 8 wt %, for example 7 wt %, referred to the total weight of the pulp material 3a, 3b. Preferably, the water content is determined by the standard EN 20638 of September 1993. The average fiber length of the pulp material 3a, 3b is preferably in the range of 0.6 mm to 6 mm. The average fiber length preferably is determined by the standard TAPPI T271 pm-91 of the year 1991.

The rough comminution 4 can for example be carried out by means of a fine gridding mill (dry mill), a cutting mill, a hammer mill, a mixer, a shredder and/or an impact mill. There is no need to use a pulper before or during the step of rough comminution 4.

After the step of rough comminution 4, the pulp material preferably is present in the form of a powder, i.e. a loose material. The water content of the pulp material after step 4 is still the same or at least not substantially greater than the one of the pulp material 3a, 3b. The average fiber length of the pulp material after the rough comminution 4 is preferably in the range of 0.025 mm-6 mm, more preferably in the range of 0.4 mm-1.7 mm Preferably, the average fiber length is preferably determined by the standard TAPPI T271 pm-91 of the year 1991.

Between the rough comminution 4 and the pre-treatment 5, it is for example possible to treat the roughly comminuted pulp material by means of TEMPO-oxidation or a carboxymethylation.

The roughly comminuted pulp material is then brought to the pre-treatment 5. During the pre-treatment 5, the pulp material is dispersed in a liquid, such as those mentioned hereinabove. It is also possible to use an enzyme during the pre-treatment 5, such as a cellulose. This dispersion comprising the pulp material and the liquid is further comminuted in the step of fine comminution 6. The fine comminution 6 can for example be carried out in a refiner, a ball mill, a homogenizer, an ultrasound device, a microfluidizer, a jet-collision device and/or a cryocrushing device. Particularly preferred is a refiner comprising cutting means made from a mineral material such as corundum, diamond or silicon carbide. Mineral materials always have a micro roughness even in case of abrasion of the cutting means. Thus, because of their permanent micro roughness, the cutting means made from mineral materials always retain their cutting abilities. In the state of the art, cutting means made of metal are used. This provides the disadvantage of metal abrasion. Metal particles are not desired in the personal care composition according to the invention.

The result of the fine comminution 6 is a mixture comprising the liquid and a fibrous material comprising micro- and/or nano-scaled fibril agglomerates. This mixture can be used as a basis to manufacture the inventive personal care composition.

The average length of the micro-scaled fibril agglomerates comprised by the fibrous material is in the range of 500 nm-1000 μm, more preferably in the range of 500 nm-600 μm, and even more preferably in the range of 500 nm-200 μm, wherein the average length is preferably determined according to standard ISO 13322-2, 1. Edition of Nov. 1, 2006 which is incorporated herein as reference.

The average length of the nano-scaled fibril agglomerates comprised by the fibrous material is in the range of 10 nm-500 nm.

The micro-scaled fibril agglomerates, as exemplary shown in FIG. 4, represent a component of the inventive personal care composition. FIG. 2 shows an exemplary view of a part of a micro-scaled fibril agglomerate which is present in the personal care composition according to the invention. The FIG. 2 is obtained by an electron microscope at a magnification of 10'000. The typical network-structure being present inside of the micro-scaled fibril agglomerate can clearly be seen. The network is formed by a plurality of fibrils which are comminuted being interconnected among each other. The part of the micro-scaled fibril agglomerate is substantially, in the view of FIG. 2, even completely, free of visible isolated fibrils, because the fibrils are only present in reduced sizes and are bound in the networks forming the micro-scaled fibril agglomerates. For comparison, in FIG. 1 conventional cellulose material produced according to a state-of-the-art method is shown at the same magnification-factor. Therein, the individual isolated fibrils are obviously visible and do not form a common network or structure. No interconnections are present between the fibrils as shown in FIG. 2. Such micro-scaled fibril agglomerates are particularly suited to produce the personal care composition according to the invention since personal care compositions produced by means of such micro-scaled fibril agglomerates are particularly are well structured and non-irritant with good drying properties.

Instead of directly using the mixture to manufacture the personal care composition, the mixture can be dried, for example thermally dried, such as spray dried, optionally under negative pressure and/or mechanically dried. These types of drying are particularly preferred since they do not negatively influence the quality of the micro-scaled and/or nano-scaled fibril agglomerates, i.e. the micro-scaled and/or nano-scaled fibril agglomerates for example do not or only slightly agglomerate themselves during the drying process. In particular, the negative influence of the drying process on the quality of the micro-scaled and/or nano-scaled fibril agglomerates can be kept low if a liquid is used for the production of the micro-scaled and/or nano-scaled fibril agglomerates which has a boiling temperature at normal pressure (101325 Pascal) of less than 100° C., more preferably a boiling temperature at normal pressure (101325 Pascal) in the range of 50° C. to less than 100° C., even more preferably in the range of 50° C. to 90° C. The boiling temperature of less than 100° C., in particular of less than 90° C., provides the advantage that the liquid can be removed from the mixture without to damage the micro-scaled and/or nano-scaled fibril agglomerates. The boiling point of at least 50° C. provides the advantage that the danger of ignition of the liquid during production is reduced. The dry mixture comprises a solids content preferably in the range of 70 wt % to 100 wt %, more preferably in the range of 80 to 97 wt %, even more preferably in the range of 85 to 95 wt %, referred to the total weight of the dry mixture.

This dry mixture can directly be used to manufacture the personal care composition according to the invention. Alternatively, the dry mixture can also be redispersed in a liquid to form a remoistened mixture. This remoistened mixture can also be used to manufacture the personal care composition. The remoistened mixture preferably comprises a solids content in the range of more than 0 wt % to 40 wt % referred to the total weight of the remoistened mixture. A remoistened mixture comprising such a solids content allows to produce a personal care composition which is well structured and non-irritant with good drying properties.

FIG. 5 shows a comparison of similar compositions with microfibrillated cellulose. The microfibrillated cellulose was obtained from different raw materials and comprises either no xylose, a small amount of xylose or a high amount of xylose. All compositions contained 1.51% microfibrillated cellulose compared to the total weight of the composition. The formulation of the compositions is as follows: 46 wt % suspension of microfibrillated cellulose (consistency of microfibrillated cellulose 3.39%, 1.51 wt % microfibrillated cellulose based on the total weight of the composition); glycerine 2 wt % (from Interchimie), 0.8 wt % preservative (Mikrokill COS from Lonza); 4 wt % emulsifier (Sepinov EMT10 from Seppic); 46 wt % water, 0.2 wt % perfume and 4 wt % argan oil.

The suspension of microfibrillated cellulose, glycerine, preservative and emulsifier were mixed until a homogenous suspension was obtained. The argan oil was added under medium stirring (500 rpm) for one minute. The water was added under high stirring (1000 rpm), followed by the perfume.

The microscope images were recorded with a Bresser LCD Microscope 9.8 cm (3.5") and a magnification of 500. The compositions were applied on microscope slides and covered with a cover slip. The black bar indicated in the right corner of each image equals 5 μm. FIG. 5A shows the respective image with microfibrillated cellulose without xylose content. The oil droplets are clearly visible and are unevenly distributed within the composition. Further, the oil droplets have different dimensions. FIG. 5B shows a composition with microfibrillated cellulose containing 8 wt % xylose. The oil droplets are more evenly distributed in the water phase compared to FIG. 5A, but are still not entirely homogenous and still different in size. In contrast, FIG. 5C, showing a respective composition with a xylose content in the microfibrillated cellulose of 15 wt % according to the invention, shows an even distribution of the oil droplets in the water with a substantially even size distribution leading to a homogenous mixture. FIG. 5D shows a composition with 20 wt % xylose, revealing a similar even distribution as shown in FIG. 5C. The composition of FIG. 5A and the composition of FIG. 5C was further subjected to a panel of 19 panelists for evaluation of the skin feel. 16 panelist out of 19 preferred composition C over A, equivalent to 84.2% preferred C over A (15.8%).

FIG. 6 shows a comparison between the composition of FIG. 5C (FIG. 6A) and a composition comprising microcrystalline cellulose (FIG. 6B) instead of microfibrillated cellulose. Measurements and concentrations are the same as defined in respect of FIGS. 5A-D. As can be derived from FIG. 6B, microcrystalline cellulose provides a composition with a less even distribution of the oil droplets in water. The oil droplets are also different in size. Thus, the composition of FIG. 6B is less homogenous compared to a composition with microfibrillated cellulose and a xylose content of 15 wt %.

In the following, examples are given how to obtain the desired personal care composition according to the present invention. These examples must be taken as a non-limiting illustration of possible ways to obtain the personal care composition according to the present invention.

EXAMPLES

In the examples, an aqueous dispersion means a dispersion of a fibrous material comprising micro-scaled and/or nano-scaled fibril agglomerates in a liquid containing water with a defined weight percentage of the fibrous material referred to the total weight of the aqueous dispersion.

Example 1: Minimalist Gel Bases

Example 1.1

0.25 wt % potassium sorbate and 0.25 wt % sorbic acid are added to 95.5 wt % of an aqueous dispersion containing 3.3 wt % (referred to the aqueous dispersion) of fibrous material comprisingmicro-scaled and/or nano-scaled fibril agglomerates. Then 1 wt % glycolic acid, 1 wt % lactic acid and 1 wt % (±)-2-hydroxyoctanoic acid and 1 wt % water-soluble collagen are dissolved in the preserved aqueous dispersion, under gentle stirring with a paddle stirrer. Then the system is let to settle until a translucent gel is formed. The level of fibrous material comprising micro-scaled and/or nano-scaled fibril agglomerates in the total composition is 3.15 wt % referred to the total weight of the composition. The sum of the weight percentages of all ingredients in the composition is 100 wt %.

Example 1.2

0.4 wt % phenoxanol and 0.2 wt % ethylglycerin are added to 96.63 wt % of the aqueous dispersion containing 3.3 wt % (referred to the aqueous dispersion) of fibrous material comprising micro-scaled and/or nano-scaled fibril agglomerates under gentle stirring. Then 2 wt % salicylic acid, 1.3 wt % (±)-2-hydroxyoctanoic acid and 0.05 wt % sodium hyaluronate are dissolved in the preserved aqueous dispersion, under gentle stirring with a paddle stirrer. Then the system is let to settle until a surfactant-free, translucent gel is formed. The level of fibrous material comprising micro-scaled and/or nano-scaled fibril agglomerates in the total composition is 3.19 wt % referred to the total weight of the composition. The sum of the weight percentages of all ingredients in the composition is 100 wt %.

Example 1.3: Minimalist Gel Base for Facial Mask 4 wt % glycerin is added to 90.6 wt % of the aqueous dispersion containing 3.3 wt % (referred to the aqueuous dispersion) of fibrous material comprising micro-scaled and/ or nano-scaled fibril agglomerates under gentle stirring. 0.4 wt % phenoxyethanol, 0.2 wt % ethylglycerin and 0.4 wt % methyl parabene are added to this mixture under gentle stirring. Then 4 wt % poly(sodium acryloyldimethyltaurate-co-vinylpyrrolidone) copolymer is added to the preceding mixture and the system is gently stirred until a homogeneous mass is obtained. Then the system is let to settle until a translucent, surfactant-free gel is formed. The level of fibrous material comprising micro-scaled and/or nano-scaled fibril agglomerates in the total composition is 3.0 wt % referred to the total weight of the composition. The sum of the weight percentages of all ingredients in the composition is 100 wt %.

Example 2: Minimalist Cream-Gel Bases

Example 2.1

2 wt % glycerin is added to 46 wt % aqueous dispersion containing 3.3 wt % (referred to the aqueous dispersion) of fibrous material comprising micro-scaled and/or nano-scaled fibril agglomerates under gentle stirring. 0.3 wt % phenoxyethanol, and 0.2 wt % ethylglycerin and 0.2 wt % methyl parabene are added to this mixture under gentle stirring. Then 1 wt % poly(sodium acryloyldimethyltaurate-co-vinylpyrrolidone) copolymer is added to the preceding mixture and the system is gently stirred until a dense homogeneous gel mass is obtained. Then 4 wt % Argan oil is added to the mass under vigorous agitation with a dissolver until a homogenous gel-like emulsion is formed. Then 46 wt % water is added to form a transluscent, surfactant-free milky cream-gel. The level of fibrous material comprising micro-scaled and/or nano-scaled fibril agglomerates in the total composition is 1.5 wt % referred to the total weight of the composition. The sum of the weight percentages of all ingredients in the composition is 100 wt %.

Example 2.2

A concentrated aqueous dispersion containing 10 wt % (referred to the concentrated aqueous dispersion) of fibrous material comprising micro-scaled and/or nano-scaled fibril agglomerates is diluted 3.85 times with deionized water under gentle stirring to obtain a diluted aqueous dispersion containing 2.6 wt % (referred to the diluted aqueous dispersion) of fibrous material comprising micro-scaled and/or nano-scaled fibril agglomerates. 97.48 wt % of this diluted aqueous dispersion is placed in a vessel. 0.5 g of collagen is added under gentle stirring until a homogeneous mass is obtained. 0.02 wt % of BRONOPOL are added to this mixture under gentle stirring. Then, 0.5 wt % of poly (sodium acryloyldimethyltaurate-co-vinylpyrrolidone) copolymer is added to the preceding mixture and the system is gently stirred until a dense homogeneous gel mass is obtained. Finally 1.5 wt % Argan oil is added to the mass under vigorous agitation with a dissolver until a homogenous gel-like emulsion is formed. The level of fibrous material comprising micro-scaled and/or nano-scaled fibril agglomerates in the total composition is 2.53 wt % referred to the total weight of the composition. The sum of the weight percentages of all ingredients in the composition is 100 wt %.

Example 3: Body Milk 0.33 wt % phenoxyethanol, 0.25 wt % ethylglycerin and 0.3 wt % methyl parabene are added to 28.5 wt % of the aqueous dispersion containing 3.3 wt % of fibrous material comprising micro-scaled and/or nano-scaled fibril agglomerates under gentle stirring. Then 0.52 wt % poly(sodium acryloyldimethyltaurate-co-vinylpyrrolidone) copolymer is added to the preceding mixture and the system is gently stirred until a dense homogeneous gel mass is obtained. Then 2.5 wt % Avocado oil and 1.5 wt % isononyl isononaoate are added to the mass under vigorous agitation with a dissolver until a homogenous gel-like emulsion is formed. Then 65.8 wt % water is added to form a translucent, surfactant-free milky cream-gel to which 0.3 wt % fragrance is added. The level of fibrous material comprising micro-scaled and/or nano-scaled fibril agglomerates in the total composition is 0.94 wt % referred to the total weight of the composition. The sum of the weight percentages of all ingredients in the composition is 100 wt %

Example 4: Sensory Results Sensory Results

A cream-gel according to example 2.2 was submitted to a panel of 16 panelists for evaluation. The test was strictly monadic and no guidance was given as of a particular way to apply the product. Freedom was given to each panelist to select a benchmark from the market place. The magnitude of each sensory attribute was evaluated on a scale from 0 (minimum) to 5 (high). The pleasantness of each sensory attribute was also evaluated on scale from 0 (unpleasant) to 5 (very pleasant). The results are reported in Table 1 and 2.

TABLE 1

Sensory assessment during application of the cream-gel

| Attribute | Magnitude | Pleasantness |
|---|---|---|
| Sample homogeneity | 5 | 5 |
| Skin penetration | 4 | 5 |
| Wet feeling | 3 | 4 |
| Cooling effect | 2 | 4 |
| Stickiness | 2 | 5 |

TABLE 2

Sensory assessment after application of the cream-gel

| Attribute | Magnitude | Pleasantness |
|---|---|---|
| Residues on skin | 2 | 5 |
| Skin appearance | 4.5 | 5 |
| Skin feel | 4 | 4 |
| Skin tightness | 0 | 4 |
| Compatibility with make-up | 5 | 5 |

The panelists selected the following benchmarks from the market place: Nivea hand cream, Nivea lotion, Avéne, Matis créme raffermissante, Lancôme Hyda Zen, Nuxe Nuxuriance Sérum Concentré, Redensifiant Antiage, Dexeryl créme.

As apparent from the sensory results in Table 1 and 2, as well as from the selection of benchmarks proposed by the panellists, the positioning of the cream-gel according to the invention in the cosmetic landscape is excellent.

The invention claimed is:

1. A personal care composition comprising, a liquid and a fibrous material of natural origin obtained from plants,
    wherein the fibrous material comprises micro-scaled and/or nano-scaled fibril agglomerates,
    wherein the micro-scaled fibril agglomerates have an average length in the range of 500 nm-1000 µm,
    wherein the nano-scale fibril agglomerates have an average length in the range of 10 nm to 500 nm, and
    wherein the fibrous material contains more than 10 wt % xylose referred to the total weight of the fibrous material.

2. The composition according to claim 1, wherein the composition is substantially free of visible isolated fibrils.

3. The composition according to claim 1, wherein the fibrous material is obtained from the Eucalyptus tree or from the beech tree.

4. The composition according to claim 1, wherein the fibrous material is obtained from chemically untreated plant pulp.

5. The composition according to claim 1, wherein the composition comprises from 0.1 to 30 wt % referred to the total weight of the composition.

6. The composition according to claim 1, comprising
    a) 0.1 to 30 wt % of the fibrous material referred to the total weight of the composition;
    b) up to 25 wt % of one or more polyols referred to the total weight of the composition;
    c) up to 5 wt % of one or more preservatives referred to the total weight of the composition;
    d) one or more functional ingredient being different from the one or more polyols mentioned under b) and different from the one or more preservatives mentioned under c); and
    e) water to complete to 100 wt %.

7. The composition according to claim 1, comprising:
a) optionally one or more preservatives; and
b) one or more functional ingredients selected from the group consisting of synthetic polymers, natural polymers, solvents, polyols, surfactants, fully or partially neutralized alpha-hydroxy acids, fully or partially neutralized beta-hydroxy acids, fully or partially neutralized dicarboxylic acids, fully or partially neutralized hyaluronic acid, C10-C24 fatty acids and their salts and their esters, C10-C24 fatty alcohols and their esters, glycerine ethoxylates, proteins and peptides, collagen, glycolipids, phospholipids, sphingolipides, sterols and steroids, allantoin, caffein, amino acids and their derivatives, quaternary amines, alkaline bases, flavonoids and isoflavonoids, polyphenols, anthocyanins, organic dyes, pigments, vitamins and their derivatives, terpenes and their derivatives, sesquiterpenes and their derivatives, triterpenes and their derivatives, ubiquinones, waxes and butters, carbohydrates and sugar alcohols, and their derivatives, mineral and vegetal particulates, bentonites, Diatomea earth, kaolin, titan dioxide; and
c) optionally one or more plant extracts, one or more plant juice, one or more essential oil and/or a perfume; and
d) water.

8. The composition according to claim 1, comprising at least one synthetic or natural hydrophilic polymer.

9. The composition according to claim 8, wherein the at least one synthetic or natural hydrophilic polymer is a copolymer or a terpolymer selected from the group comprising vinylpyrrolidone/acrylate copolymers, copolymers and cross-polymers derived from alkyl (meth)acrylates, (meth)acrylic acids and acrylamidodimethyltauric acid and their salts, vinylpyrrolidone/acrylamido alkylsulphonic acid copolymers; xanthan gum, dehydro-xanthan gum, guar gum, gum Arabic, Accacia gum, Sclerotium gum, Ceratonia siliqua gum; pullulans, glycans, glycoaminoglycanes, carraghenans, alginates, pectins, hyaluronic acid and its salts, sodium hyaluronate cross-polymers, chitosan, and mixtures thereof; and wherein the level of the polymer in the composition is in the range of 0.05 and 10 wt % referred to the total weight of the composition.

10. The composition according to claim 1, comprising at least one polyol, wherein the level of the at least one polyol in the composition is in the range of 0.5 to 50 wt % referred to the total weight of the composition.

11. The composition according to claim 1, comprising at least one oil, wherein the level of the at least one oil in the composition is in the range of 0.5 to 50 wt % referred to the total weight of the composition.

12. The composition according to claim 1, comprising one or more surfactant(s).

13. A method to produce a personal care composition comprising a liquid and a fibrous material of natural origin obtained from plants, comprising at least the steps of
a) comminuting dry pulp by mechanical means;
b) dispersing said comminuted pulp in a liquid; and
c) further comminuting the pulp dispersed in the liquid to form a mixture comprising the liquid and the fibrous material comprising micro-scaled and/or nano-scaled fibril agglomerates, wherein the micro-scaled fibril agglomerates have an average length in the range of 500 nm-1000 µm, and wherein the nano-scale fibril agglomerates have an average length in the range of 10 nm to 500 nm;
wherein the fibrous material contains more than 10 wt % xylose referred to the total weight of the fibrous material.

14. The method according to claim 13, comprising the additional step of:
d) adding at least one functional ingredient to the mixture.

15. The method according to claim 13, wherein in step a) the dry pulp is comminuted without the substantial addition of a liquid.

16. The composition according to claim 1, wherein the micro-scaled fibril agglomerates have an average length in the range of 500 nm to 600 µm.

17. The composition according to claim 1, wherein the fibrous material contains more than 15 wt % xylose referred to the total weight of the fibrous material.

18. The composition according to claim 3, wherein the fibrous material is obtained from the Eucalyptus Urograndis tree.

19. The composition according to claim 5, wherein the composition comprises from 0.5 to 20 wt % of the fibrous material referred to the total weight of the composition.

20. The method according to claim 13, wherein in step c), the pulp is further comminuted by means of a mineral material.

* * * * *